US012011160B2

(12) United States Patent
Epstein et al.

(10) Patent No.: US 12,011,160 B2
(45) Date of Patent: *Jun. 18, 2024

(54) MINIMALLY-INVASIVE TISSUE SUTURING DEVICE

(71) Applicant: ANCHORA MEDICAL LTD., Yokneam (IL)

(72) Inventors: Jonatan Epstein, Ramat Hasharon (IL); Avraham Rami Lore, Kiryat Tivon (IL); Rotem Baavour, Regavim (IL); Gonen Yuval, Kiryat Tivon (IL); Ohad Cohen, Haifa (IL); Amir Richtman, Karkur (IL)

(73) Assignee: ANCHORA MEDICAL LTD., Yokneam (IL)

(*) Notice: Subject to any disclaimer, the term of this patent is extended or adjusted under 35 U.S.C. 154(b) by 175 days.

This patent is subject to a terminal disclaimer.

(21) Appl. No.: 17/720,540

(22) Filed: Apr. 14, 2022

(65) Prior Publication Data

US 2022/0240925 A1 Aug. 4, 2022

Related U.S. Application Data

(63) Continuation of application No. 16/349,271, filed as application No. PCT/IL2017/051234 on Nov. 13, 2017, now Pat. No. 11,304,691.

(Continued)

(51) Int. Cl.
*A61B 17/04* (2006.01)
(52) U.S. Cl.
CPC .......... *A61B 17/0469* (2013.01); *A61B 17/04* (2013.01); *A61B 17/0401* (2013.01);
(Continued)

(58) Field of Classification Search
CPC . A61B 17/0469; A61B 17/04; A61B 17/0401; A61B 2017/0409;
(Continued)

(56) References Cited

U.S. PATENT DOCUMENTS 4,823,794 A 4/1989 Pierce
5,041,129 A 8/1991 Hayhurst et al.
(Continued)

FOREIGN PATENT DOCUMENTS

AU 2007200095 A1 3/2007
CA 2949363 A1 11/2015
(Continued)

OTHER PUBLICATIONS

David J.Desilets et al, "Loop-anchor purse-string versus endoscopic clips for gastric closure: a natural orifice transluminal endoscopic surgery comparison study using burst pressures", Gastrointestinal Endoscopy, Dec. 2009, vol. 70 issue 6, pp. 1225-1230.

(Continued)

*Primary Examiner* — Kelly J Bekker
*Assistant Examiner* — Andrew P. Restaino
(74) *Attorney, Agent, or Firm* — The Roy Gross Law Firm, LLC; Roy Gross

(57) ABSTRACT

An apparatus for suturing tissue, comprising: a needle having a beveled opening and housing multiple anchors, wherein each of said anchors comprises an elongated tubular body and a loop connected to said tubular body, and wherein a thread is threaded sequentially through the loops; and a pushrod configured to push each of said anchors towards the opening of said needle, to extract each respective anchor from the opening.

14 Claims, 21 Drawing Sheets

Related U.S. Application Data

(60) Provisional application No. 62/421,319, filed on Nov. 13, 2016.

(52) U.S. Cl.
CPC ............ *A61B 2017/0409* (2013.01); *A61B 2017/0414* (2013.01); *A61B 2017/0417* (2013.01); *A61B 2017/0464* (2013.01)

(58) Field of Classification Search
CPC .... A61B 2017/0414; A61B 2017/0417; A61B 2017/0464
See application file for complete search history.

(56) References Cited

U.S. PATENT DOCUMENTS

| | | | |
|---|---|---|---|
| 5,782,866 A | 7/1998 | Wenstrom, Jr. | |
| 5,791,022 A | 8/1998 | Bohman | |
| 5,810,848 A | 9/1998 | Hayhurst | |
| 5,948,002 A | 9/1999 | Bonutti | |
| 6,007,566 A | 12/1999 | Wenstrom, Jr. | |
| 6,719,763 B2 | 4/2004 | Chung et al. | |
| 6,755,843 B2 | 6/2004 | Chung et al. | |
| 6,966,916 B2 | 11/2005 | Kumar | |
| 6,988,987 B2 | 1/2006 | Ishikawa et al. | |
| 7,534,248 B2 | 5/2009 | Mikkaichi et al. | |
| 7,674,275 B2 | 3/2010 | Martin et al. | |
| 7,704,261 B2 | 4/2010 | Sakamoto et al. | |
| 7,780,702 B2 | 8/2010 | Shiono | |
| 7,815,662 B2 | 10/2010 | Spivey et al. | |
| 7,998,150 B2 | 8/2011 | Shiono et al. | |
| 8,021,376 B2 | 9/2011 | Takemoto et al. | |
| 8,105,342 B2 | 1/2012 | Onuki et al. | |
| 8,128,657 B2 | 3/2012 | Shiono et al. | |
| 8,231,640 B2 | 7/2012 | Hayashi et al. | |
| 8,287,556 B2 | 10/2012 | Gilkey et al. | |
| 8,317,679 B2 | 11/2012 | Surti | |
| 8,376,932 B2 | 2/2013 | Hashiba et al. | |
| 8,377,095 B2 | 2/2013 | Surti et al. | |
| 8,540,735 B2 | 9/2013 | Mitelberg et al. | |
| 8,551,139 B2 | 10/2013 | Surti et al. | |
| 8,679,136 B2 | 3/2014 | Mitelberg | |
| 8,702,753 B2 | 4/2014 | Mikkaichi et al. | |
| 8,771,314 B2 | 7/2014 | Crombie et al. | |
| 8,777,964 B2 | 7/2014 | Onishi et al. | |
| 8,911,454 B2 | 12/2014 | Hayashi et al. | |
| 9,089,325 B2 | 7/2015 | Mitelberg et al. | |
| 9,198,562 B2 | 12/2015 | Mitelberg et al. | |
| 9,198,648 B2 | 12/2015 | Crombie et al. | |
| 9,986,996 B2 | 6/2018 | Hiernaux et al. | |
| 10,245,169 B2 | 4/2019 | Hiernaux et al. | |
| 2002/0019649 A1 | 2/2002 | Sikora et al. | |
| 2002/0087178 A1 | 7/2002 | Nobles et al. | |
| 2002/0188301 A1 | 12/2002 | Dallara et al. | |
| 2003/0120287 A1 | 6/2003 | Gross et al. | |
| 2004/0002734 A1* | 1/2004 | Fallin ................ | A61B 17/0401 606/232 |
| 2004/0122474 A1 | 6/2004 | Gellman et al. | |
| 2004/0210241 A1 | 10/2004 | James et al. | |
| 2004/0249395 A1 | 12/2004 | Mikkaichi et al. | |
| 2005/0251207 A1 | 11/2005 | Flores et al. | |
| 2005/0261710 A1 | 11/2005 | Sakamoto et al. | |
| 2005/0283192 A1 | 12/2005 | Torrie et al. | |
| 2006/0178680 A1 | 8/2006 | Nelson et al. | |
| 2006/0293710 A1 | 12/2006 | Foerster et al. | |
| 2007/0027476 A1 | 2/2007 | Harris et al. | |
| 2007/0049929 A1 | 3/2007 | Catanese et al. | |
| 2007/0051377 A1 | 3/2007 | Douk | |
| 2007/0060929 A1 | 3/2007 | Onishi et al. | |
| 2007/0112385 A1 | 5/2007 | Conlon | |
| 2007/0112425 A1 | 5/2007 | Schaller et al. | |
| 2007/0185530 A1 | 8/2007 | Chin-Chen et al. | |
| 2007/0198000 A1 | 8/2007 | Miyamoto et al. | |
| 2008/0045976 A1 | 2/2008 | Gibbons et al. | |
| 2008/0051655 A1 | 2/2008 | Sato et al. | |
| 2008/0234729 A1 | 9/2008 | Page et al. | |
| 2008/0243148 A1 | 10/2008 | Mikkaichi et al. | |
| 2008/0243150 A1 | 10/2008 | Starksen et al. | |
| 2009/0082786 A1 | 3/2009 | Surti | |
| 2009/0088797 A1 | 4/2009 | Crombie et al. | |
| 2009/0259232 A1 | 10/2009 | Shiono et al. | |
| 2010/0030263 A1 | 2/2010 | Cheng et al. | |
| 2010/0049212 A1 | 2/2010 | Caborn et al. | |
| 2010/0057124 A1 | 3/2010 | Triel et al. | |
| 2010/0113873 A1 | 5/2010 | Suzuki et al. | |
| 2010/0121355 A1 | 5/2010 | Gittings et al. | |
| 2011/0071549 A1 | 3/2011 | Cabom et al. | |
| 2011/0071551 A1 | 3/2011 | Singhatat et al. | |
| 2011/0172682 A1 | 7/2011 | Brady et al. | |
| 2012/0035654 A1 | 2/2012 | Belson | |
| 2012/0326118 A1 | 12/2012 | Nitta | |
| 2013/0253574 A1 | 9/2013 | Catanese, III et al. | |
| 2014/0128914 A1 | 5/2014 | Deitch | |
| 2014/0148828 A1 | 5/2014 | Ewers et al. | |
| 2015/0032133 A1 | 1/2015 | Ferlin et al. | |
| 2015/0190129 A1 | 7/2015 | Nelson et al. | |
| 2015/0190173 A1 | 7/2015 | Hiernaux et al. | |
| 2015/0250470 A1 | 9/2015 | Vargas | |
| 2015/0257751 A1 | 9/2015 | Bachar | |
| 2016/0242761 A1 | 8/2016 | Lore et al. | |
| 2018/0153539 A1 | 6/2018 | Motai et al. | |
| 2020/0129173 A1 | 4/2020 | Hiernaux et al. | |

FOREIGN PATENT DOCUMENTS

| | | |
|---|---|---|
| EP | 2581046 A1 | 4/2013 |
| FR | 2731610 A1 | 9/1996 |
| JP | 2006239455 A | 9/2006 |
| JP | 2008237645 B2 | 12/2010 |
| JP | 2010246941 A | 11/2011 |
| WO | 2011010011 A1 | 1/2011 |
| WO | 2012096280 A1 | 7/2012 |
| WO | 2013114347 A1 | 8/2013 |
| WO | 2013131023 A2 | 9/2013 |
| WO | 2014033692 A2 | 3/2014 |

OTHER PUBLICATIONS

John R Romanelli et al, "Loop-Anchor Purse-String Closure of Gastrotomy in Notes (R) Procedures: Survival Studies in a Porcine Model", Surgical Innovation, Dec. 2010, 17(4), pp. 312-317.
M S Zeichen et al, "Closure versus non-closure of hernia defect during laparoscopic ventral hernia repair with mesh"; Hernia,; vol. 17, issue 5, pp. 589-596, Jun. 20, 2013.
PCT International Search Report for International Application No. PCT/IL2017/051234, dated Mar. 4, 2018, 5pp.
PCT Written Opinion for International Application No. PCT/IL2017/051234, dated Mar. 4, 2018, 5pp.
PCT International Preliminary Report on Patenability for International Application No. PCT/IL2017/051234, dated May 14, 2019, 6pp.

\* cited by examiner

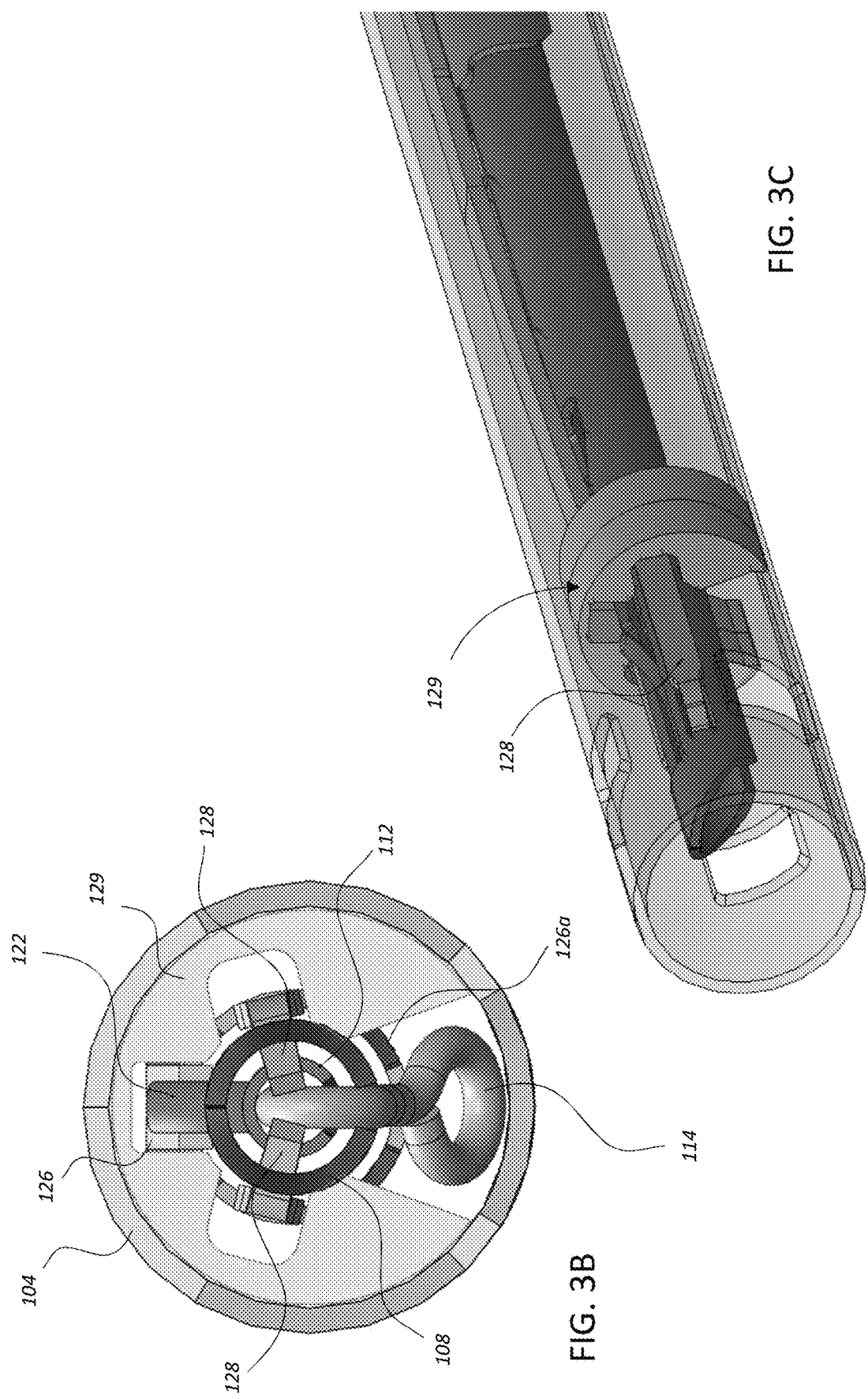

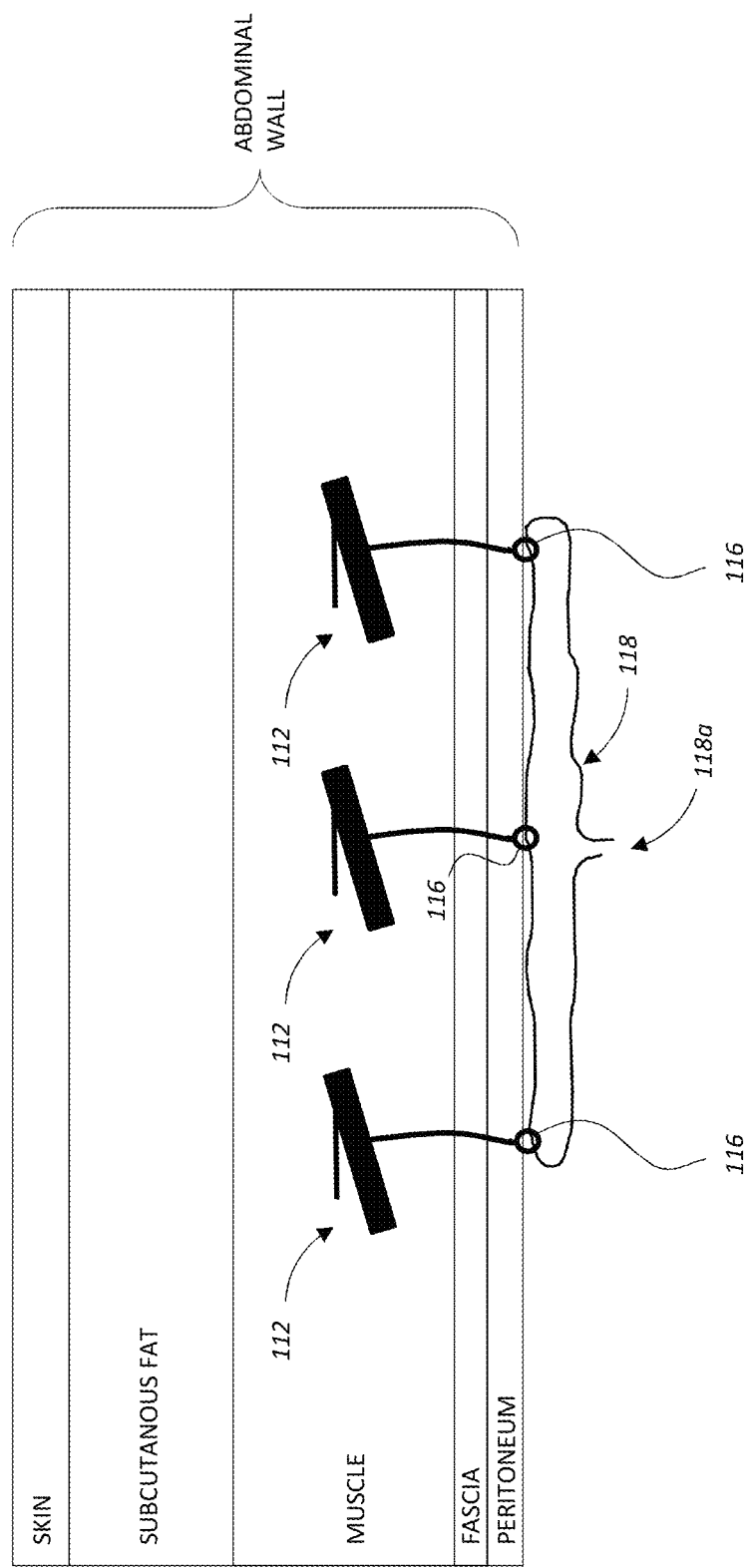

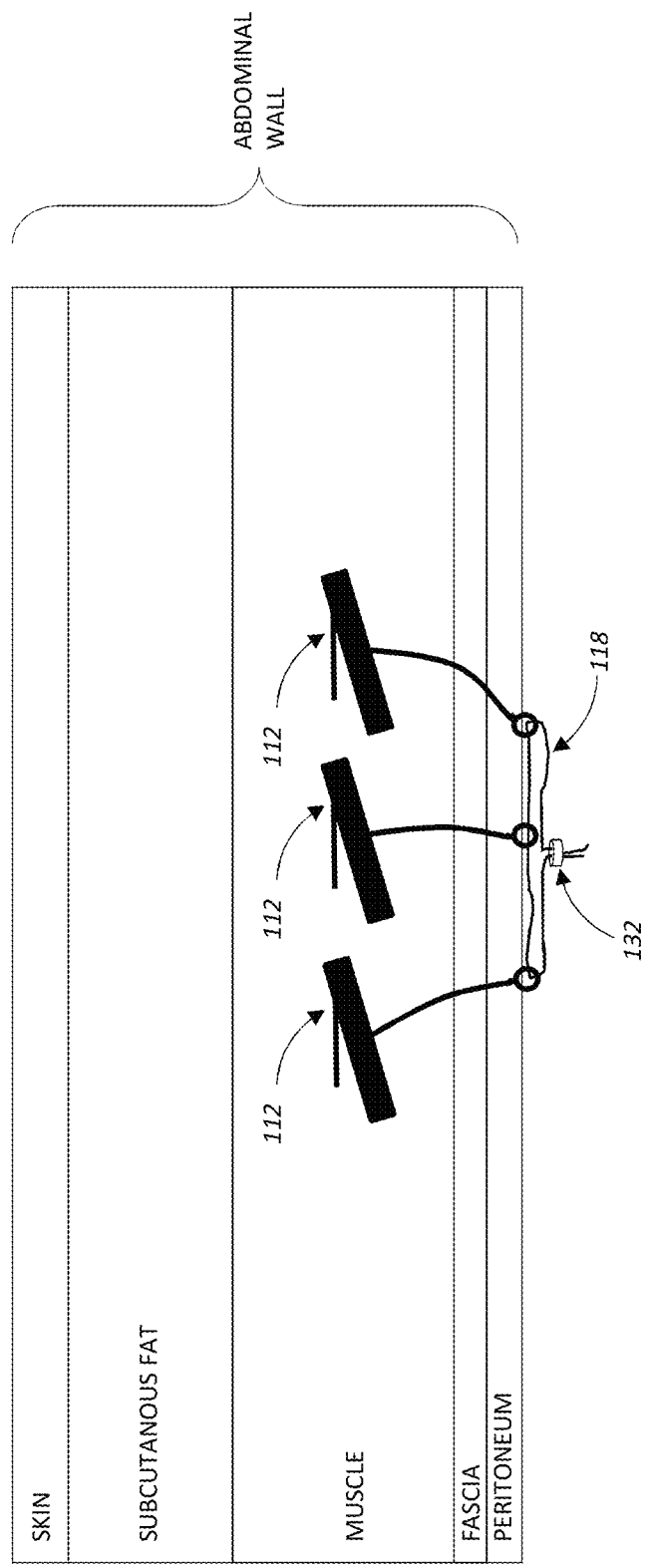

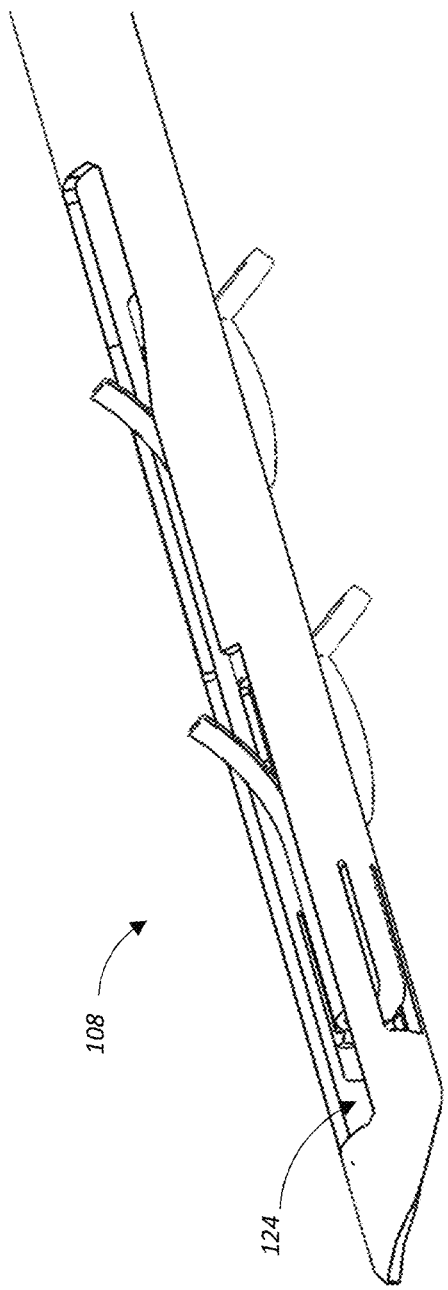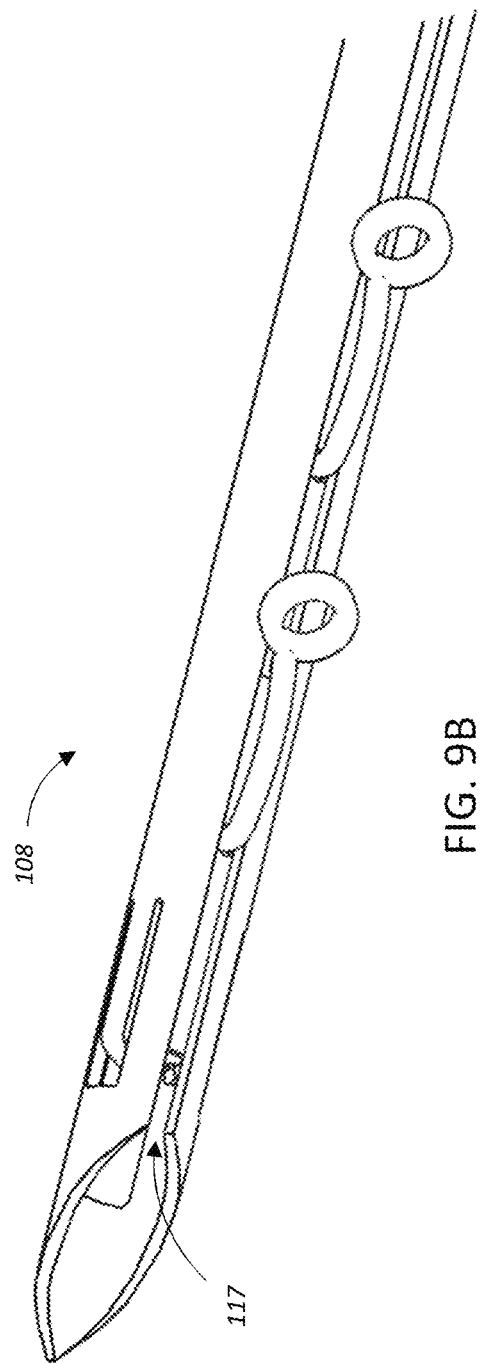
FIG. 9A
FIG. 9B

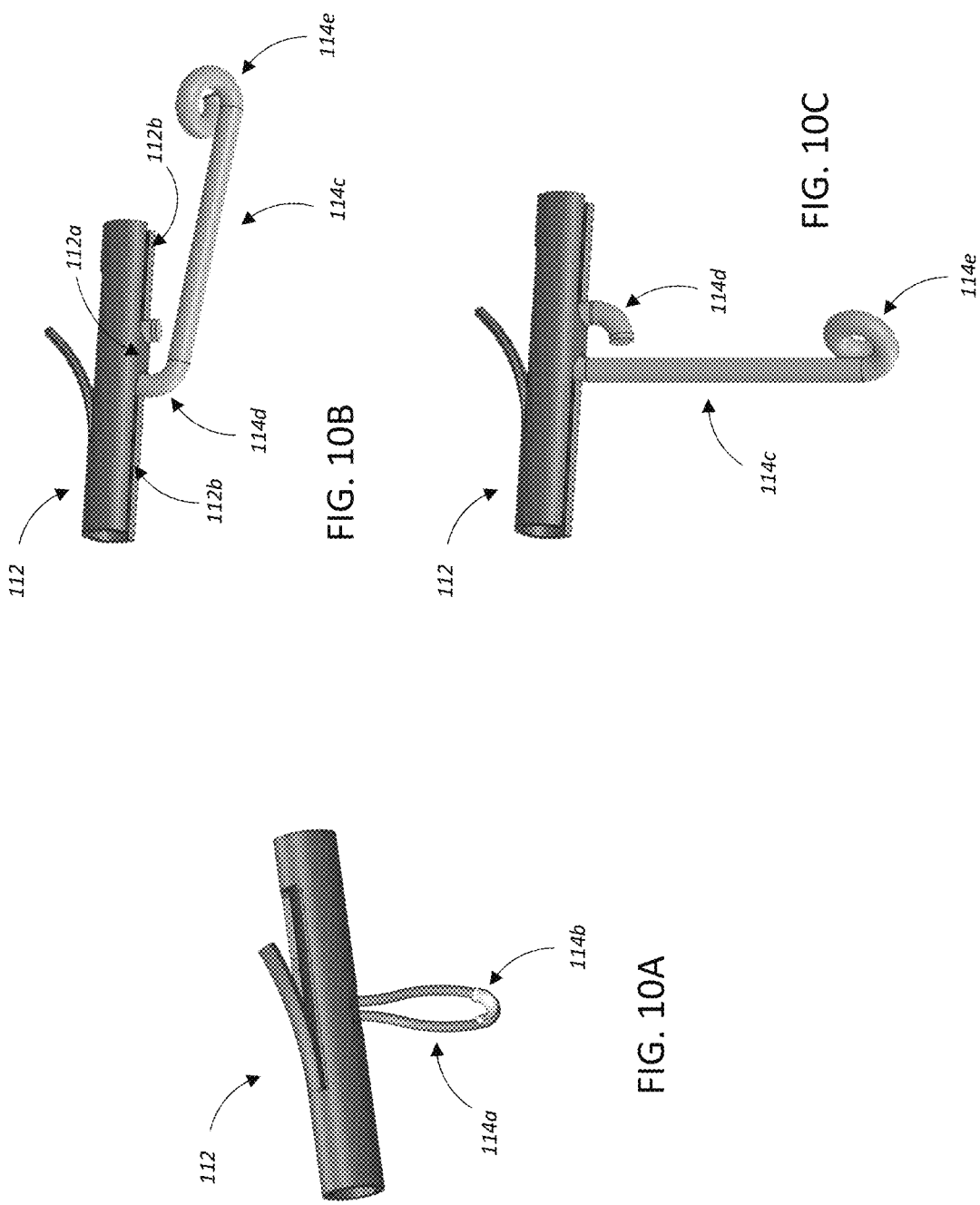

MINIMALLY-INVASIVE TISSUE SUTURING DEVICE

CROSS-REFERENCE TO RELATED APPLICATIONS

This application is a continuation of U.S. patent application Ser. No. 16/349,271, filed May 12, 2019, which is a National Phase of PCT Patent Application No. PCT/IL2017/051234 having International filing date of Nov. 13, 2017, which claims the benefit of priority to U.S. Provisional Patent Application No. 62/421,319, filed Nov. 13, 2016, entitled "Minimally-Invasive Tissue Suturing Device", the contents of which are all incorporated herein by reference in their entirety.

BACKGROUND

The invention relates to the field of suturing devices.

Suturing remains a common approach for repair of live tissue and is used for tissue closure, approximation, ligation and fixation of tissue access sites, organs, vessels, fixation of meshes and other implants or devices and the like. Although largely dependent on the skill of the surgeon, the results obtained using a suture are highly predictable and reliable.

Alternatives to suturing developed over the years such as staples, fasteners (also known as "tacks"), anchors, and tissue adhesives, have gained varying degrees of acceptance and are used for tissue repair in both open and minimally invasive procedures. Nonetheless, suturing remains ubiquitous in surgical repair due to availability of a wide variety of suturing kits at relatively low costs and the mechanical advantages afforded by suturing.

Thus, suture remains a mainstay of surgical repair however, it is not without disadvantages. Placing a number of stitches can be tiring and time-consuming which can lead to suturing errors that can compromise the integrity of repair. In addition, manipulation of a suture needle as well as access to the suturing location can be difficult especially in minimally invasive surgery due to the nature of the minimally invasive surgery and/or the limited anatomical space around the target tissues, while tying knots with a desired amount of tension requires precise manipulation of the suture ends further complicating and slowing open, and in particular, minimally-invasive surgeries. In fact, for many procedures the time spent suturing may be significantly greater than the time spent treating the underlying target tissues.

In some ventral and incisional hernia cases, where the defect is relatively large (for example over a few centimeters), it is common practice not to suffice with mesh reinforcement but also to physically suture ("close") the abdominal wall at the site of the defect. The closure may be done extracorporeally or intracorporeally. Closure of such defects is known to significantly decrease the reoccurrence of the hernia, relative to reinforcement with just a mesh. For example, Zeichen et al. (2012) showed that recurrence rates were threefold lower when closure was done in addition to mesh reinforcement. See Zeichen et al., "Closure Versus Non-closure of Hernia Defect During Laparoscopic Ventral Hernia Repair With Mesh", SAGES Abstracts, 2012.

FIGS. 1A, 1B, and 1C show three stages of hernia defect closure with mesh reinforcement, in accordance with prior art. FIG. 1A illustrates the large hernia defect in a cross-sectional view. FIG. 1B shows a top view of the defect being sutured in extracorporeal approach, after a mesh has already been affixed. FIG. 1C shows the final state, after the suture has been tensioned and knotted, and the mesh deployed and affixed underneath the fascia.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

Some embodiments are directed to an apparatus for suturing tissue, comprising: an elongated shaft; a hollow needle disposed inside said elongated shaft, said needle having: an elongated slit which opens to a distal end of said needle, and an aperture disposed at a distal area of said needle; a handle disposed at a proximal end of said elongated shaft; multiple anchors disposed in a single file inside said needle, along the length of said needle, wherein each of said multiple anchors comprises: an elongated tubular body, a loop connected to said tubular body and exiting said needle through said elongated slit to a space between said needle and an inner wall of said elongated shaft, a fin emerging outwardly from said elongated tubular body, wherein a free end of said fin points toward the proximal end of said elongated shaft, and wherein the fin of the most distal anchor in the single file protrudes from said needle through said aperture; a thread disposed along the length of said elongated shaft, in the space between said needle and said inner wall of said elongated shaft, and threaded sequentially through said loops of said anchors; and a pushrod disposed in the space between said needle and said inner wall of said elongated shaft, wherein said pushrod is triggerable by said handle to push the fin of the most distal anchor in the single file, thereby to eject the most distal anchor in the single file from a distal opening of said needle.

In some embodiments, said loop is a cord emerging from an outer wall of said elongated tubular body, and terminating with a ring.

In some embodiments, said loop is a rigid wire having a proximal curl secured to said anchor, a straight section, and a distal curl through which said thread is threaded.

In some embodiments, the apparatus further comprises a push tube disposed inside the elongated shaft and over the needle, wherein the pushrod is attached to a distal end of said push tube, and wherein the triggering of the pushrod is by pushing said push tube distally.

In some embodiments, said handle comprises a trigger connected to a proximal end of said push tube.

In some embodiments, said pushrod is flexible and bends when passing through said aperture to push said fin.

In some embodiments, said fin emerges from said elongated tubular body opposite said loop.

In some embodiments, said handle is configured to allow said elongated shaft to retract into said handle while maintaining said needle stationary, so that a distal area of said needle is exposed and penetrates tissue.

In some embodiments, said handle comprises a shaft blocking lever that is movable between a position that blocks backwards movement of said shaft and a position that allows backwards movement of said shaft.

In some embodiments, said handle comprises a spool of thread.

In some embodiments, said handle comprises a trigger that is connected to said pushrod.

In some embodiments, the apparatus further comprises a push tube disposed inside the elongated shaft and over the needle, wherein the pushrod is attached to a distal end of said push tube, and wherein the triggering of the pushrod is by pushing said push tube distally; and a trigger comprised in said handle, wherein said trigger is connected to said push tube, such that depressing said trigger pushes said push tube distally.

Some embodiments are directed to an apparatus for suturing tissue, comprising: a needle having a beveled opening and housing multiple anchors, wherein each of said anchors comprises an elongated tubular body and a loop connected to said tubular body, and wherein a thread is threaded sequentially through the loops; and a pushrod configured to push each of said anchors towards the opening of said needle, to extract each respective anchor from the opening.

In some embodiments, each of said anchors further comprises a fin emerging outwardly from said elongated tubular body, wherein said pushrod is configured to push each of said fins towards the opening of said needle.

In some embodiments, said pushrod is sized to push each of said fins until the respective anchor completely exits the opening of said needle.

In some embodiments, the apparatus further comprises an elongated shaft, wherein said needle is disposed inside said elongated shaft.

In some embodiments, the apparatus further comprises a handle disposed at a proximal end of said elongated shaft.

In some embodiments, the apparatus further comprises a pushrod disposed in a space between said needle and said inner wall of said elongated shaft, wherein said pushrod is triggerable by said handle to push the fin of the most distal anchor in the single file, thereby to eject the most distal anchor in the single file from a distal opening of said needle.

In some embodiments, the apparatus further comprises a push tube disposed inside the elongated shaft and over the needle, wherein the pushrod is attached to a distal end of said push tube, and wherein the triggering of the pushrod is by pushing said push tube distally.

In some embodiments, said handle comprises a trigger that is connected to a proximal end of said push tube.

In some embodiments, said needle has an aperture disposed at a distal area of said needle, said pushrod is flexible and bends when passing through said aperture to push said fin, and the fin of the most distal anchor in the single file protrudes from said needle through said aperture.

In some embodiments, said needle has an elongated slit which opens to a distal end of said needle.

In some embodiments, said loop exits said needle through said elongated slit to a space between said needle and an inner wall of said elongated shaft.

In some embodiments, said fin emerges from said elongated tubular body opposite said loop.

In some embodiments, said handle is configured to allow said elongated shaft to retract into said handle while maintaining said needle stationary, so that a distal area of said needle is exposed and penetrates tissue.

In some embodiments, said handle comprises a shaft blocking lever that is movable between a position that blocks backwards movement of said shaft and a position that allows backwards movement of said shaft.

In some embodiments, said handle comprises a spool of thread.

Some embodiments are directed to a method for closing an opening in a tissue, comprising: sequentially deploying anchors in the tissue, around the opening, wherein: (a) each of the anchors comprises an elongated tubular body, a loop connected to said tubular body, and a fin emerging outwardly from said elongated tubular body opposite said loop, (b) a thread is threaded through the loops of the anchors, and (c) the loops are partially exposed from the tissue, and the thread is completely exposed from the tissue; and pulling the thread, thereby approximating the loops, approximating the anchors, and closing the opening in the tissue.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 3B is a distal-to-proximal view of the distal portion of the shaft, in accordance with an embodiment;

FIG. 3C is a semi-transparent perspective view of the distal portion of the shaft, in accordance with an embodiment;

FIG. 6A is a cross-sectional illustration of an abdominal wall with three anchors disposed therein, in accordance with an embodiment;

FIG. 6B is a cross-sectional illustration of the abdominal wall after a thread has brought the three anchors closer together to close a defect, in accordance with an embodiment;

FIGS. 9A-9B are perspective view of a needle of the apparatus, in accordance with an embodiment;

FIG. 10A is a perspective view of an anchor, in accordance with an embodiment;

FIGS. 10B and 10C are perspective views of another anchor, in accordance with an embodiment;

DETAILED DESCRIPTION

Disclosed herein is an apparatus for suturing tissue, and a method for suturing tissue using the apparatus. The apparatus may be used, for example, for minimally-invasive hernia defect closure during a laparoscopic ventral hernia repair (LVHR) procedure.

Alternatively, the apparatus may be used for a different suturing task, such as, but not limited to, closing a laparotomy incision or performing other intracorporeal approximation or fixation. For reasons of simplicity, the disclosure describes the apparatus and method in relation to closure of a hernia defect, but those of skill in the art will recognize that these descriptions may apply, mutatis mutandis, to other suturing tasks.

Advantageously, the apparatus deploys multiple anchors that are structured in a way that: (a) prevents or mitigates damage to surrounding tissue, (b) allows the tissue to be closed by a convenient and simple pulling of a thread, after the anchors have been deployed satisfactorily, (c) enables strong fixation while not protruding outside the body, thus reducing risk of infection, (d) reduces tension on the sutured tissue (compared with regular, manual suturing) and thus reduces the risk of tissue trauma and thread 'cheese cuts', (e) does not form a loop that encapsulates tissue, and thus decreases the risk for nerve entrapment and reduction of blood flow to the encapsulated tissue, (f) enforces standardized suturing thus reduces the variability between surgeons of different skill levels, (g) reduces hernia recurrence rates while simplifying the procedure, (h) divides tension between all anchors, (i) when tensioning the thread, reduces friction of the thread with the anchor, by concentrating the friction of the thread on a smooth ring or loop, and (j) reduced the amount of artificial material that remains exposed from the tissue after the procedure, thus reducing adhesion risks. Namely, the apparatus facilitates the convenient formation of a continuous suture.

Figure 1C:
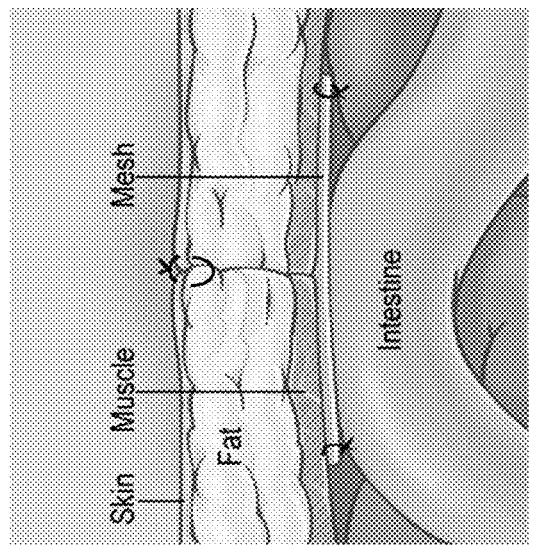
FIGS. 1A, 1B, and 1C show three stages of hernia defect closure with mesh reinforcement, in accordance with prior art.
Figure 1B:
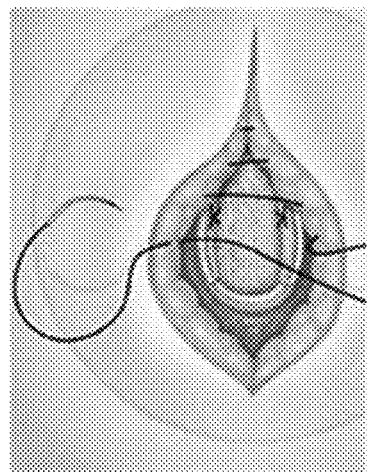
Figure 1A:
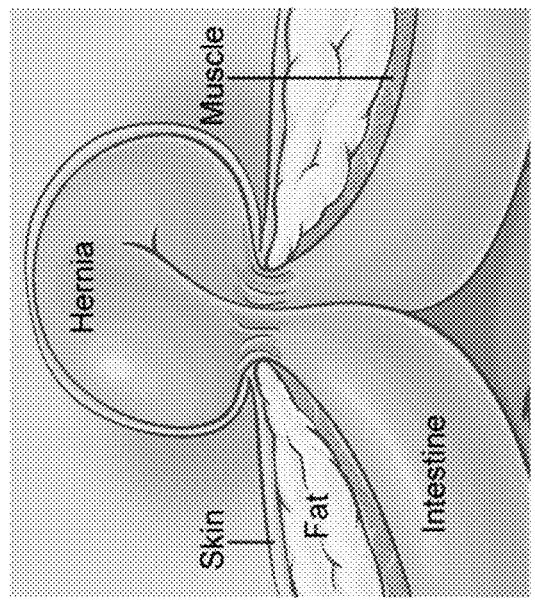
Figure 2A:
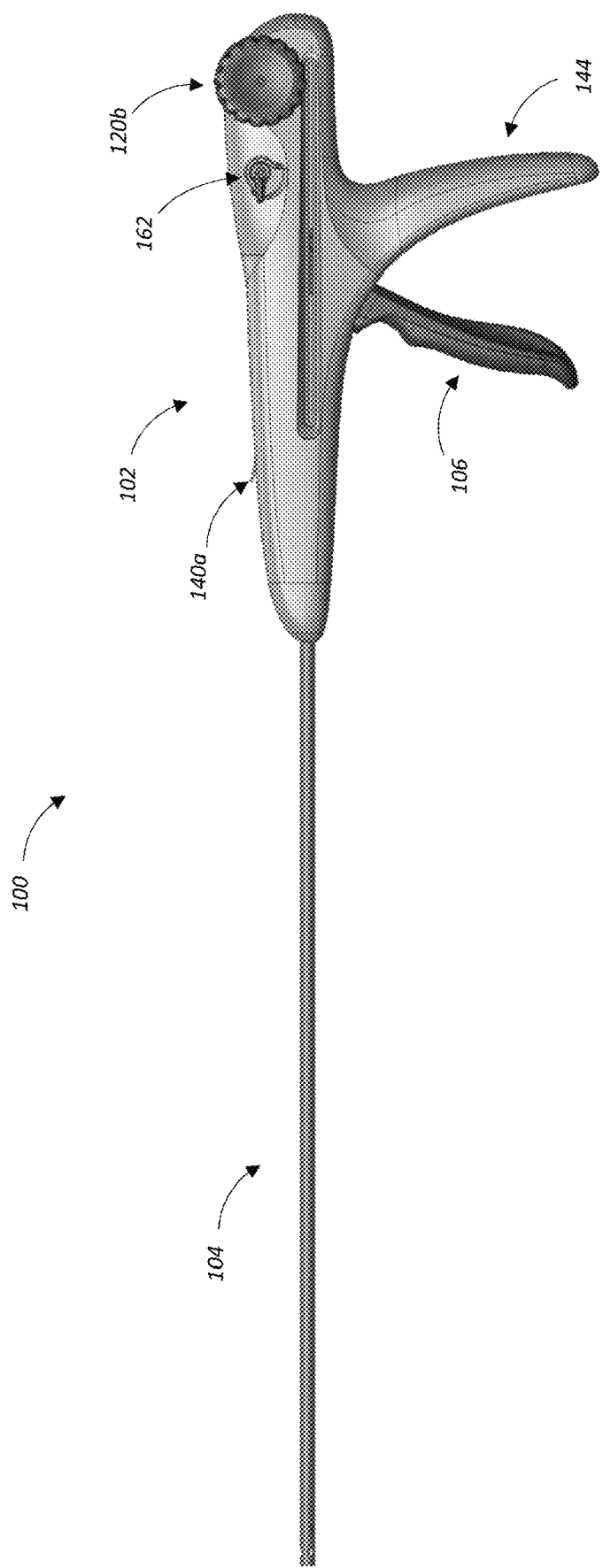
FIG. 2A is a side view of an apparatus for suturing tissue, in accordance with an embodiment.
Figure 2B:
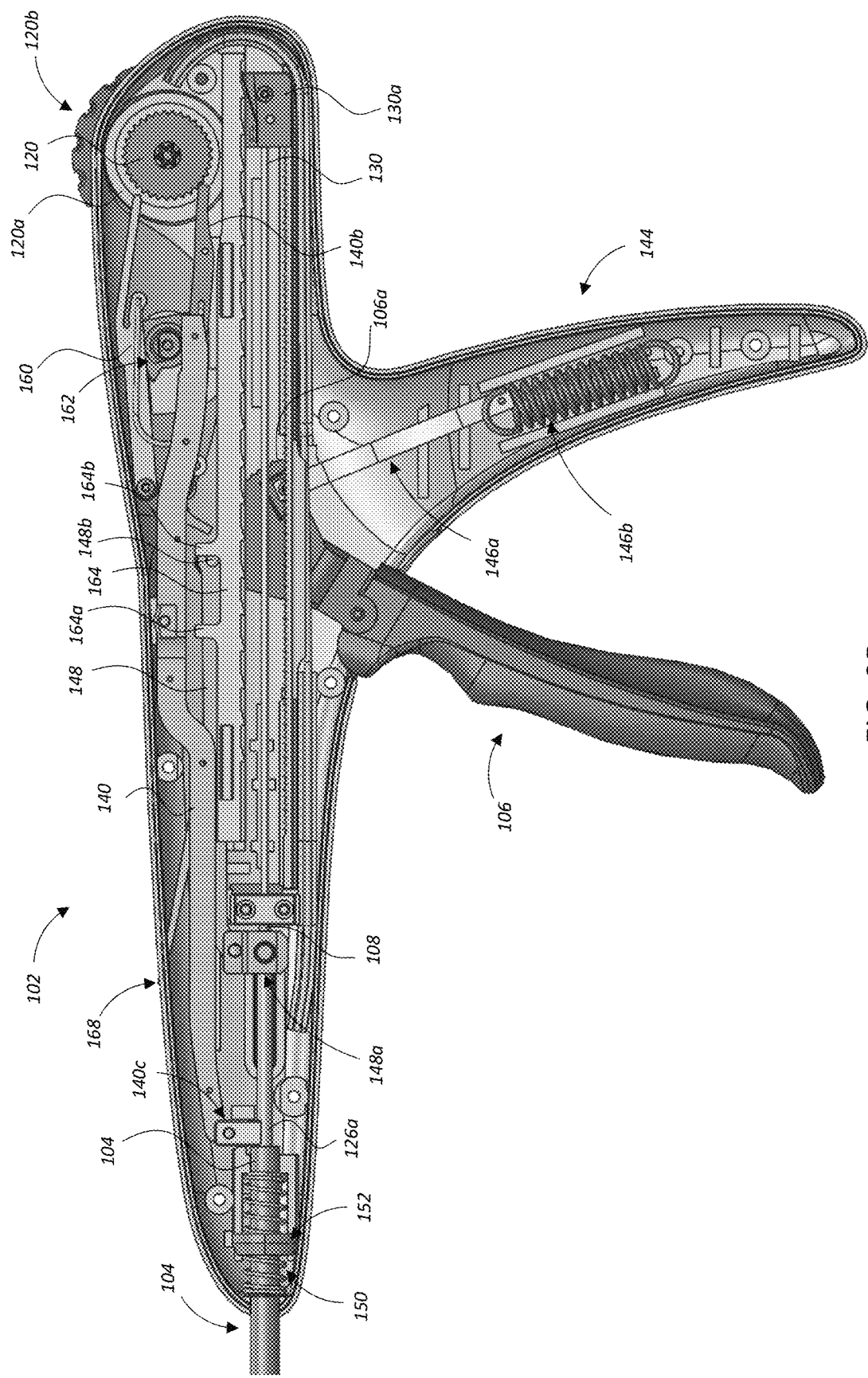
FIG. 2B, 2C and 2D are semi-transparent views of the apparatus for suturing tissue, in accordance with an embodiment.

Reference is now made to FIGS. 2A and 2B, which show a side view and a semi-transparent view, respectively, of an apparatus 100 for suturing tissue, in accordance with an embodiment. Apparatus 100 generally includes a handle 102 and an elongated shaft 104. Only a proximal portion of shaft 104 is shown in FIG. 2B. Those of skill in the art will recognize that the apparatus may be readily adapted for use by a surgical robot; for example, the various physical actuators included in the handle may be structured in a way that allows electromechanical actuators of the robot to manipulate them.

Figure 4A:
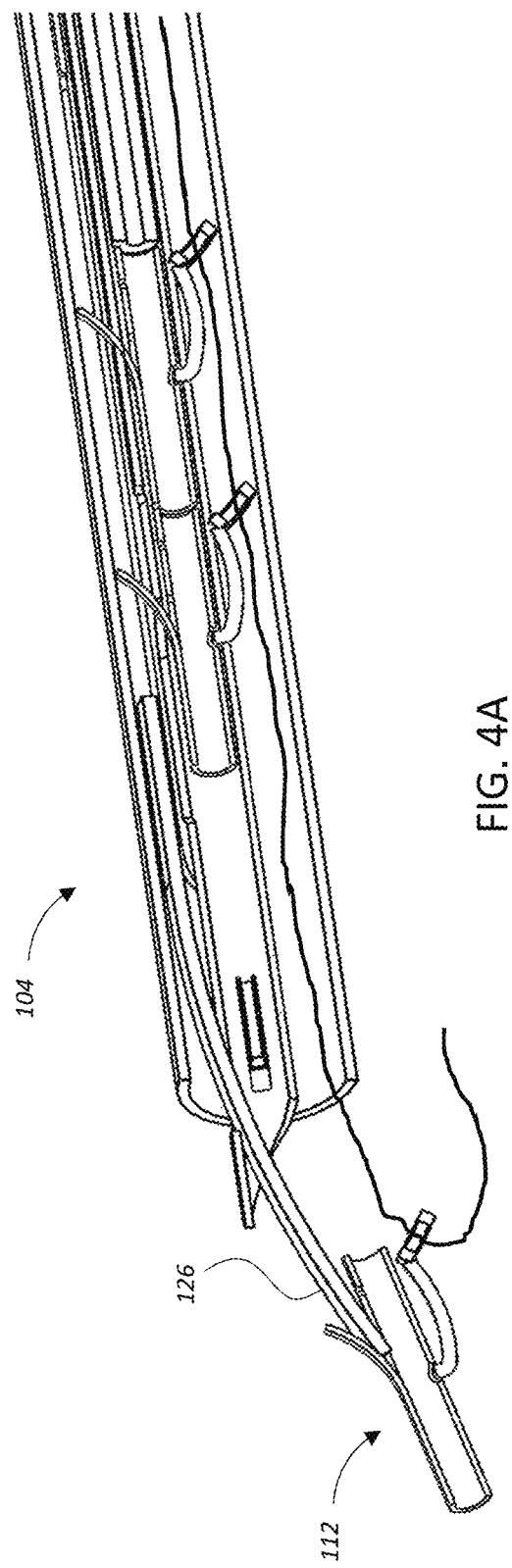
FIGS. 4A, 4B, and 4C are a cross-section view and two side views, respectively, of the distal portion of the shaft during deployment of an anchor, in accordance with an embodiment.
Figure 4B:
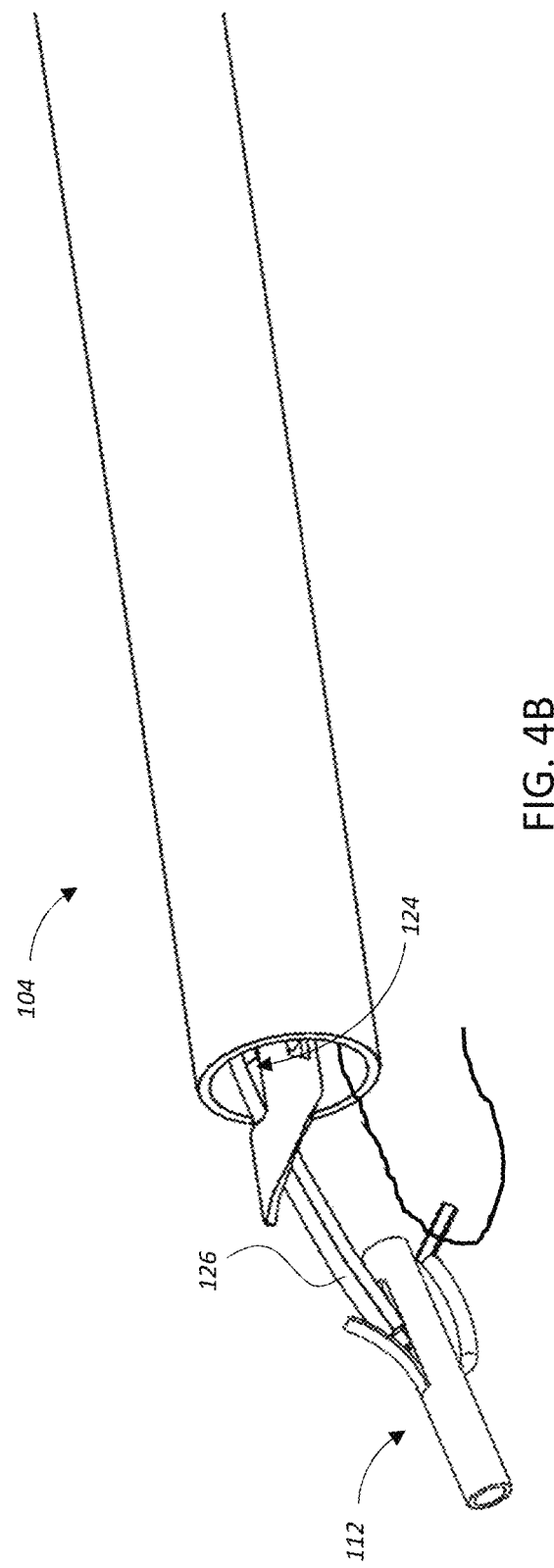
Figure 4C:
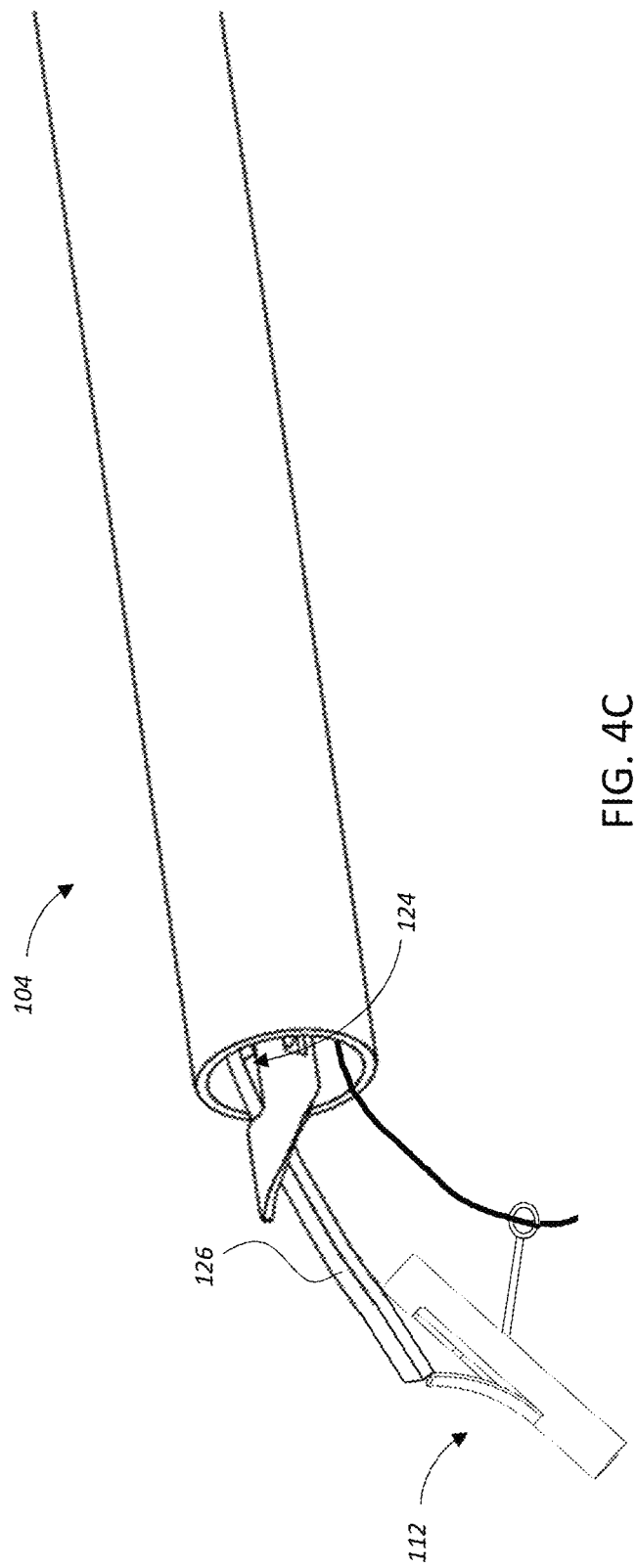
Figure 5:
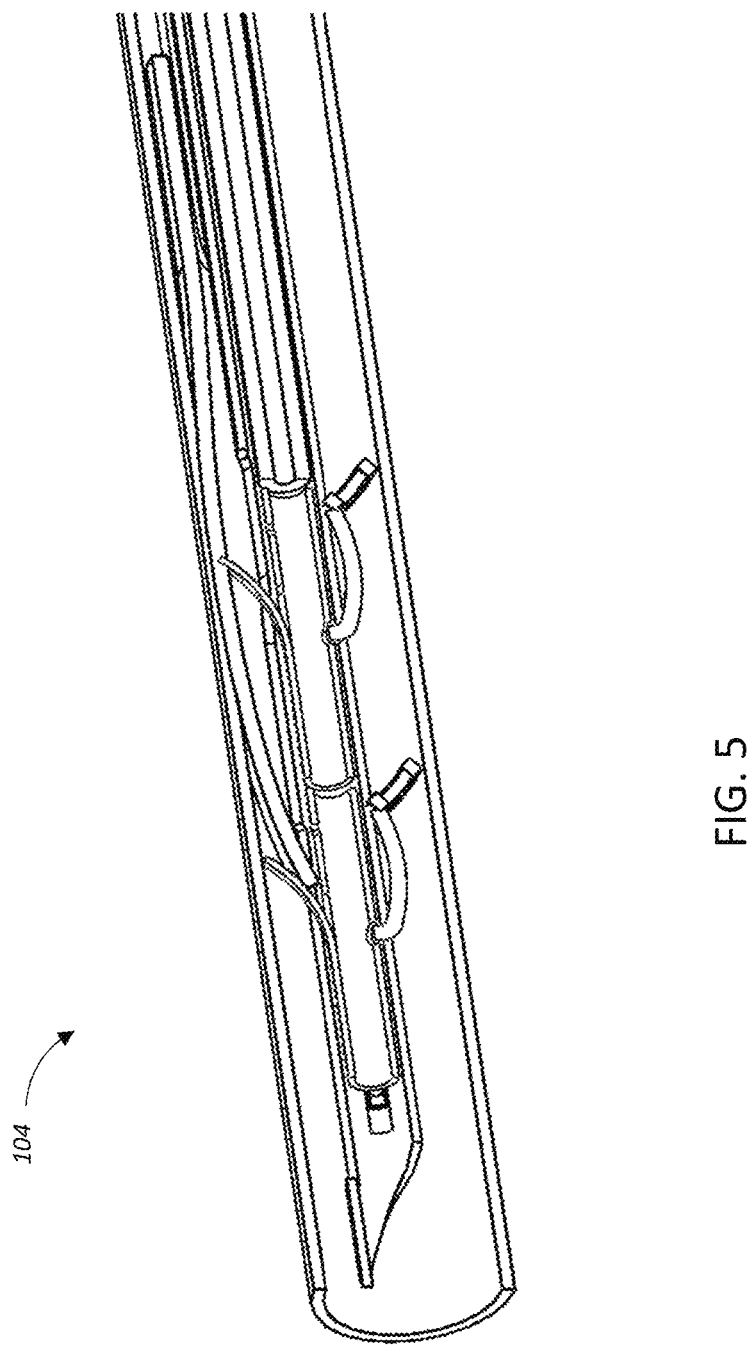
FIG. 5 is a cross-sectional view of the distal portion of the shaft after the deployment of the anchor, in accordance with an embodiment.

Reference is also made to FIGS. 3-5, which show a distal portion of shaft 104 in various stages of the operation of apparatus 100. Shaft 104 may have a length of, for example, 50-700 millimeters (mm), wherein part of this length is inside handle 102. Shaft 104 may have an external diameter of, for example, 2 to 10 mm, and a wall thickness of, for example, 0.2 to 0.6 mm. Shaft 104 may have a uniform or a variable diameter along its length.

Handle 102 may include one or more user-operable actuators, such as, but not limited to, a trigger 106, a cam shaft 162, and a spool 120a. These user-operable actuators may serve to activate an anchor advancement mechanism disposed in handle 102 and/or in shaft 104, whose role is to deploy multiple anchors from apparatus 100 into tissue.

Shaft 104 may be an elongated tube, either (a) rigid (for use in laparoscopic procedures), (b) rigid with a bended angle or flexible (for use in either laparoscopic or endoscopic procedures), or (c) rigid with controllable articulation capabilities—either at one or more manipulatable joints, or along entire segment(s) of the shaft. Shaft 104 may be made, for example, of plastic and/or metal.

A hollow needle 108 having a sharp (optionally beveled) edge 110 may be disposed inside shaft 104 longitudinally. Needle 108 may have the same length as shaft 104 or a different length. Needle 108 may have an external diameter of, for example, 0.8 to 5 mm, and a wall thickness of, for example, 0.2 to 0.6 mm. Shaft 104 may have a uniform or a variable diameter along its length. Needle 108 may be made of stainless steel or any other suitable material. There may be one needle inside the shaft or multiple needles (shown on page 1 of Appendix A). In the case of multiple needles, each may be used to deploy a single anchor, or, alternatively, each may be used to deploy multiple anchors.

Needle 108 optionally has a longitudinal slit 117 which extends from edge 110 to either a proximal edge (not shown) of the needle, or less than that. Slit 117 is shown as continuous slit, but in other embodiments it may be divided into multiple slits along the length of needle 108. Slit 117 may be, for example, 0.1 to 1 mm wide. Its width may be uniform of variable along its length.

Optionally, needle 108 has one or more apertures 124 in its wall, that are optionally disposed on a side of the wall opposite slit 117. If multiple apertures are present, such as a frontal aperture 124a and a dorsal aperture 124b, they may be equidistantly or non-equidistantly disposed.

FIGS. 9A-9B are top and bottom perspective views of needle 108, in which slit 117 and aperture 124 are more clearly visible.

Optionally, needle 108 has one or more anchor stoppers 128, embodied as resilient protrusions from an inner wall of the needle into the lumen of the needle—thus decreasing the inner diameter of the needle at that location. Stoppers 128 may normally protrude into the lumen of needle 108, but may be pushed completely or partially out of the lumen when an anchor (further discussed below) applies on it a sufficient amount of force. Stopper 128 may be constructed such that it can resist a predetermined amount of force.

Multiple anchors 112 may be disposed in a single file inside needle 108. Each of anchors 112 may have an elongated tubular body made of a rigid material, such as stainless steel, nitinol (nickel-titanium alloy), and/or plastic (permanent, such as polyether ether ketone, or bioabsorbable, such as poly(lactic-co-glycolic acid)). The tubular body may have a diameter of, for example, 0.5-3 millimeters (mm), a wall thickness of, for example, 0.05 to 0.4 mm, and a length of, for example, 2-15 mm. Alternatively, the anchor may have a solid cylindrical body, or have a different shape which is substantially elongated, such as a rectangular box or the like.

A loop may be connected to, attached to, or integrally formed with the tubular body of anchor 112, such as a loop of wire or a different material. For example, the loop may be embodied as a cord 114 that emerges from the outer wall of each anchor 112. Cord 114 may be a surgical thread (sometimes referred to as a "surgical suture"), or a flexible or rigid rod (straight, curved, spring-coiled, etc.) made of a suitable material such as stainless steel, nitinol, plastic, etc. Cord 114 is optionally also tensile, with such tensile strength allowing up to approximately 20% to 100% elongation without plastic deformation. Such tensile properties of cord 114 may further reduce tension from the tissue in which anchor 112 is implanted, when the thread is pulled and tensioned. Cord 114 may have a circular profile or a non-circular profile. Cord 114 may be attached to, connected to, or integrally formed with anchor 112. Cord 114 may have a diameter of, for example, 0.1-2 mm, which may be uniform of variable along its length. Optionally, cord 114 is doubled over itself, such that there are in fact two cord segments extending between the outer wall of anchor 112 and a ring, which is described below. Cord 114 may be attached to, connected to, or integrally formed with anchor 112.

Cord 114 may terminate with a ring 116, or, alternatively, with a similarly-functional closed structure (not shown) that allows a thread to pass therethrough. Optionally, ring 116 is smooth and lacks any sharp edges, thus preventing or mitigating damage to the thread from friction with the ring. Ring 116 may be made of a rigid or flexible material, such as stainless steel, nitinol, or plastic. Ring 116 may be attached to, connected to, or integrally formed with cord 114. Cord 114 may be rotatable around its longitudinal axis, to prevent thread loops (a thread 118 is discussed below) over ring 116.

Alternatively, as shown in FIG. 10A, anchor 112 may have a loop of suture 114a, optionally with a protective cover 114b at its middle, to lower friction with thread 118.

Further optionally, as shown in FIGS. 10B and 10C, anchor 112 may have a rigid wire 114c as its loop. Wire 114c may be straight along most of its length, except in its (a) proximal area 114d, where it curls to form an arc of at least 250 degrees, the arc encircling a bridge 112a between two opposing elongated slits 112b in the tubular body of the anchors, (b) distal area 114e, where it curls helically or to about 360 degrees or more, such that the thread can pass inside this curl without escaping. If using a thicker thread, the curl may form an arc of less than 360 degrees, such as between 270 and 350 degrees. When anchor 112 is inside the needle, wire 114c may assume the position shown in FIG. 10B—substantially parallel to the longitudinal axis of anchor 112. When anchor 112 is deployed in tissue and the thread is tensioned, wire 114c may assume the position shown in FIG. 10C—substantially perpendicular to the longitudinal axis of anchor 112. Rigid wire 113c is optionally made of stainless steel, and has a diameter of between 0.2 to 1 mm, or more specifically 0.3 to 0.7 mm. The curl at the distal area 114e of rigid wire 113c is optionally tilted away from the anchor, so as to allow free pass of the thread through the loops of the anchors when the cord lies substantially parallel to the anchor inside the shaft. The tilting is optionally of an angle between 10 and 45 degrees, but could be to a greater or lesser angle.

Figure 10G:
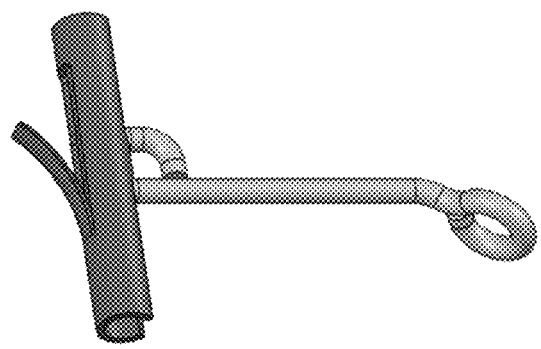
FIGS. 10D, 10E, 10F, and 10G are perspective views of a further anchor, in accordance with an embodiment.
Figure 10F:
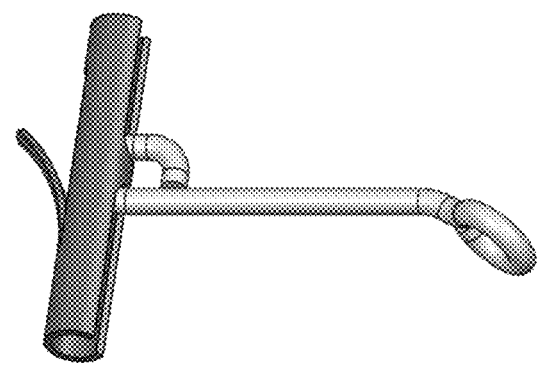
Figure 10D:
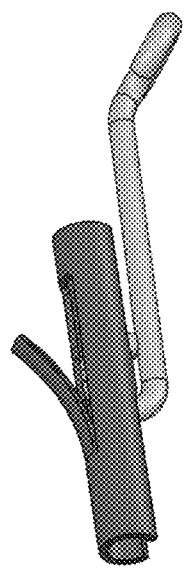
Figure 10E:
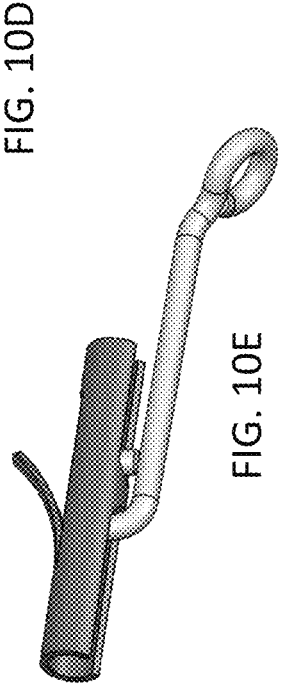

FIGS. 10D-10G show a variant of the anchor of FIGS. 10B-10C, in which the rigid wire has a different configuration in its proximal and distal areas. In the proximal area, the wire has a closed or a nearly closed arc, namely—the distal end of the wire contacts or almost contacts the outer surface of the straight section of the wire. In the distal area, the wire forms a non-helical loop that is closes or nearly closed. FIGS. 10D-10E show the anchor with its wire positioned substantially parallel to the anchor, which is the posture the anchor assumes when it is inside the needle. 10F-10G show the anchor with its wire positioned substantially perpendicular to the anchor, which is the posture the anchor assumes when it is within tissue.

Figure 10H:
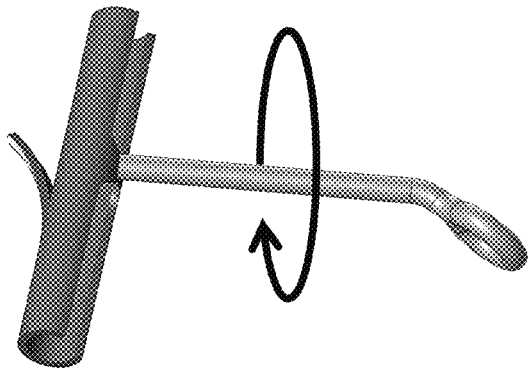
FIG. 10H is a perspective view of a further anchor, in accordance with an embodiment.

FIG. 10H shows a further variant of the previously-shown anchors, in which the rigid wire is threaded, in its proximal area, through an aperture in the wall of the anchor. A bulge or a bend (not shown) at the proximal end of the wire prevents it from falling through the aperture. This wire is therefore able to rotate along its length axis, as the arrow shows. This may become useful after the anchor is implanted in tissue and the thread tensioned—the thread will rotate the distal loop of the wire to a position where there is the least amount of tension on the loop. This may lower the probability of disintegration of the wire due to the tension applied by the thread. In this variant of the anchor, the wire may also be flexible, so that it may resiliently lie flush with the anchor when inside the needle, and move angularly to the anchor after being extracted from the needle.

The elongated tubular body of anchor 112 may have a protrusion from its outer wall, which protrusion is disposed, for example, opposite where cord 114 emerges from the anchor. An exemplary protrusion is shown in the figures as a flexible or rigid fin 122, which is a cutout in the wall of anchor 112. When anchor 112 is made of a memory shape material, such as nitinol, fin 122 may be trained to protrude and emerge from the wall of the anchor. A free end 122a of fin 122 may point towards a proximal end of shaft 104. When anchor 112 is in a position inside needle 108 where an aperture 124 is present, fin 122 may protrude away from the wall of the anchor, through the aperture. When anchor 112 is in a position inside needle 108 where no aperture is present, fin 122 may resiliently flatten, to lie flush with the wall of the anchor's tubular body. As an alternative to a fin which is cut out of the anchor body, another fin (now shown) may be attached or connected to the anchor body. As a further alternative, there may be, for example, multiple fins (e.g., 2-6) that are disposed in different radial locations on or in the anchor body. Fin 122 may, for example, have a sharp free end, a blunt free end, or a toothed free end, etc.

A thread 118 may be disposed inside shaft 104, along the length of the shaft, and optionally exiting a distal end 104a of the shaft. Thread 118 may be threaded sequentially through rings 116 of anchors 112. Thread 118, at its proximal area, is optionally wound around a spool 120 disposed in handle 102. Thread 118 may be disposed inside the shaft so both ends are proximally located in the handle 102 or outside the handle, generating a thread loop inside apparatus 100.

Thread 118 is optionally a surgical thread (sometimes referred to as a surgical "suture"), which may be bioabsorbable or non-bioabsorbable. Suitable bioabsorbable materials include, for example, polyglycolic acid, polylactic acid, monocryl, and polydioxanone. Suitable non-bioabsorbable materials include, for example, nylon, polyester, PVDF (Polyvinylidene fluoride), and polypropylene. Thread 118 may be a braided thread, a monofilament line, or a multifilament line. Thread 118 be made of metal or plastic, or of any biocompatible material. Thread 118 may be rigid or tensile.

Advantageously, the fact the present thread is not threaded through the bodies of the anchors but rather through the rings or loops that are distanced from the anchor bodies and are not embedded into tissue, prevents the thread from applying force to the tissue, which may, in extreme cases, even cut the tissue.

Furthermore, when the present thread is tensioned to finally close the tissue, the distancing of the rings from the anchor bodies reduces stress from the anchor bodies and concentrates that stress at the rings, and slightly along the cords.

Further yet, the use of anchors implies that there is a greater surface area implanted in the tissue and opposing forces which attempt to extract the anchors from the tissue. If only a suture were used, the only surface area securing the suturing were that the suture itself—which is very little.

In addition, the rings (or any other structure through which the thread is threaded) are structured such that they impose as little friction as possible on the thread. This way, when the thread is tensioned and secured, and following the entire recovery period, the rubbing of the thread over the rings' surface does not tear or otherwise degrade the thread.

An elongated pushrod 126 may be disposed along the length of shaft 104, and be structured and disposed such that it terminates behind fin 122 of the distalmost anchor of the multiple anchors 112, and can be advanced distally to push the distalmost anchor out of needle 108.

Pushrod 126 may be a rigid rod which optionally has a bend whose convexity is pointed towards the inner wall of shaft 104, or a flexible rod that is capable of bending similarly. Alternatively, the pushrod may be rigid and straight, and have a downwards protrusion at its distal end, that can be positioned behind the fin of the distalmost anchor (this configuration is not shown). In FIGS. 3-4, the bend is visible in the section of pushrod 126 which extends from a distal end of the pushrod to approximately the middle of the most proximal anchor 112. This is merely one example; the bend in pushrod 126 may have such length, convexity and resiliency to allow it to push a distalmost anchor 112, by its fin 122a, out of needle 108, to a sufficient distance away from edge 110 of the needle such that the anchor tilts inside the tissue, until finally settling in the tissue approximately perpendicularly to the length axis of shaft 104. The term "approximately perpendicularly" refers to an angle of 30 to 110 degrees, optionally 60 to 110 degrees. Optionally, the bend (and optionally other segment(s)) of pushrod 126 is resilient, such that when it is not biased by an external force (its delimitation between needle 108 and the inner wall of shaft 104), it resiliently moves downwards and furthers the tilting of the distalmost anchor 112. Pushrod 126 or at least its bend may be made of an elastic or superelastic metal, nitinol, or an elastomer.

Pushrod 126 may be sized so at to fit through the distalmost aperture 124 in needle 108. This way, the distal end of pushrod 126, when pushed distally, follows fin 122 into the lumen of needle 108, and continues to move in a downwards direction to facilitate the tilting of the distalmost anchor 112. Pushrod 126 may be linked to handle 102 via an optional push tube 126a, which is disposed inside shaft 104 and over needle 108. Push tube 126a may terminate before apertures 124, and pushrod 126 may be attached to an outer surface of the push tube, at the distal area of the push tube. When handle 102 is utilized to push push tube 126a distally, it in turn moves pushrod 126 distally. As an alternative to push tube 126a, the pushrod may extend all the way into the handle, in the space between the needle and the shaft (this configuration is not shown).

Pushrod 126 may either be the sole element responsible to deploy anchors 112 to their final location in the tissue, or be aided by a further element: an optional second elongated pushrod 130 ("advancer rod") which may be embodied as a rod disposed inside needle 108, pushing anchors 112 from behind. When apparatus 100 includes advancer rod 130, pushrod 126 may serve to push anchor 108 only slightly out of shaft 104 (e.g., until a proximal end of that anchor is 5 to 10 mm away from distal opening 104a of the shaft), and provide the anchor with an initial tilt in a direction opposite the pushrod. In FIGS. 3-5, this direction is downwards. The initial tilt may be to an angle of, for example, 5 to 30 degrees from the original posture of anchor 112 inside needle 108. Then, advancer rod 130 continues to push that anchor 112 distally by pushing the anchors behind it, until the anchor is positioned sufficiently deep in the tissue (for example, between 5 mm and 30 mm inside the tissue). Due to the initial tilt of anchor 108, the tensioning of thread 118 towards the handle, and the continued linear pushing by advancer rod 130, anchor 108 continues to tilt as it penetrates deeper into the tissue, until it assumes an approximately perpendicular position.

As briefly discussed above, an anchor advancement mechanism may be disposed in handle 102 and/or in shaft 104, whose role is to deploy multiple anchors 112 from apparatus 100 into tissue. The term "anchor advancement mechanism" is meant to refer to those particular parts of apparatus 100 that: push needle 108 distally, to expose a distal portion thereof out of distal end (also "opening) 104a of shaft 104, and retract the needle back into the shaft (or, alternatively, retract the shaft while keeping the needle stationary, thereby exposing the distal portion of the needle); and push anchors 112 one at a time, to eject then out of distal end 110 of needle 108. The anchor advancement mechanism may be triggerable by handle 102, for example by having a user, such as a surgeon, operate one or more of the user-operable actuators, such as, but not limited to, trigger 106.

Figure 3A:
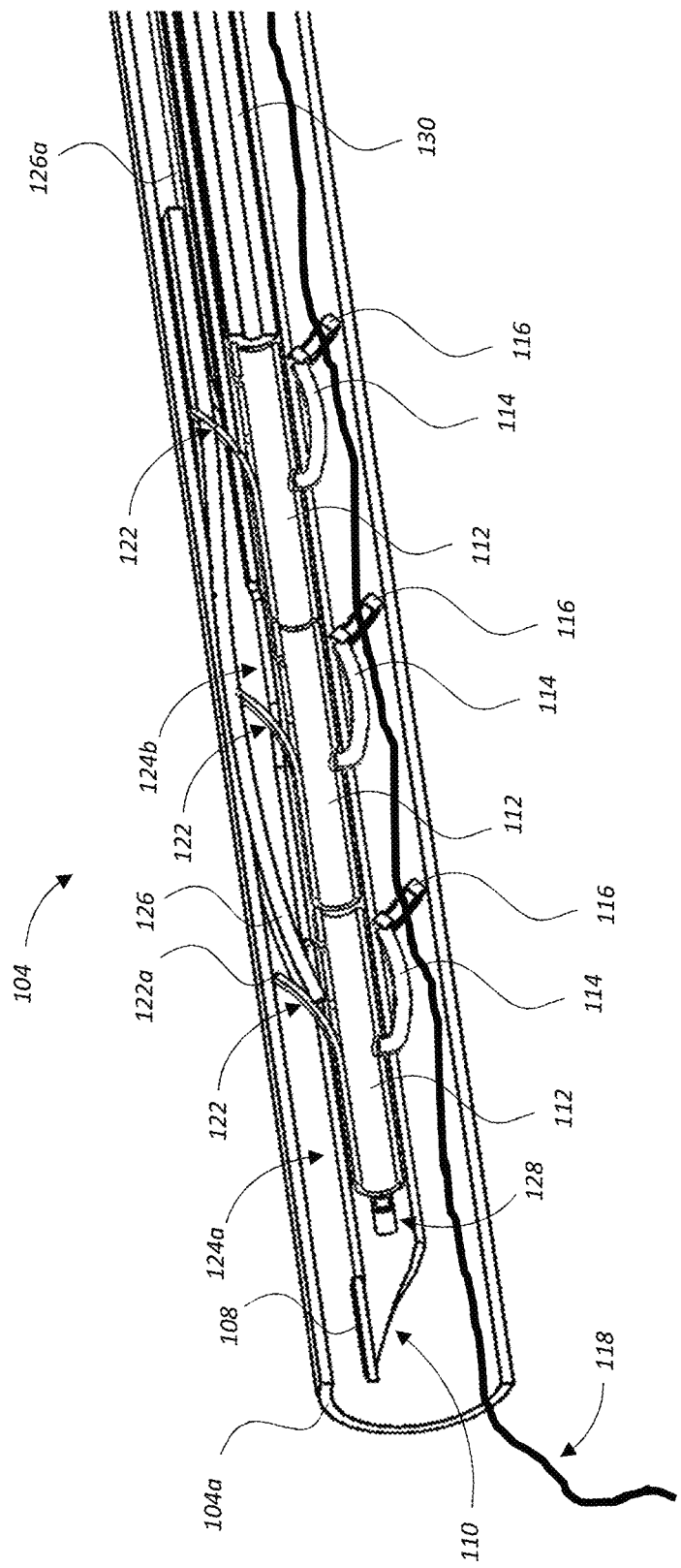
FIG. 3A is a cross-sectional view of a distal portion of a shaft of the apparatus, in accordance with an embodiment.

FIG. 3B shows a distal-to-proximal view of shaft 104, in which anchor 112, fin 122, cord 114, needle 108, push tube 126a, pushrod 126, and anchor stoppers 128 are visible. Also shown in this figure is a spacer 129, which was omitted from FIG. 3A for better clarity of other elements. Spacer 129 may have the general shape of a disc, whose outer perimeters is in contact with the inner wall of shaft 104. The disc has multiple cutouts that accommodate needle 108, the loops, fins 122, and pusher 116. This is better shown in FIG. 3C, which is a perspective view of a distal area of shaft 104.

In an embodiment, the apparatus lacks a needle, and the anchors are disposed directly inside the shaft. For example, the shaft may have an internal structure with spaces (e.g., interconnected lumens) for the single file of anchors, the fins, the pushrod that pushes the fins, and the loops.

In an embodiment, the apparatus lacks a shaft, and the needle is the outermost tube extending from the handle and inserted into the surgical site.

Apparatus 100 may be operated per the following method. This method is discussed as a laparoscopic one, but those of skill in the art will recognize that the same techniques may apply, mutatis mutandis, in medical procedures in which suturing is done not via laparoscopy.

With reference to FIG. 2B, apparatus 100 may be held by a grip 144 of handle 102. Apparatus 100 may be pushed such that shaft 104 is introduced into a patient's abdomen through a small (e.g., 2-15 mm) incision. Shaft 104 may be either directly inserted through the incision, or indirectly through a trocar or another port. Alternatively, shaft 104 may be inserted through a natural orifice, with or without a later incision made to penetrate from the lumen of the natural orifice into a desired surgical area.

Figure 2C:
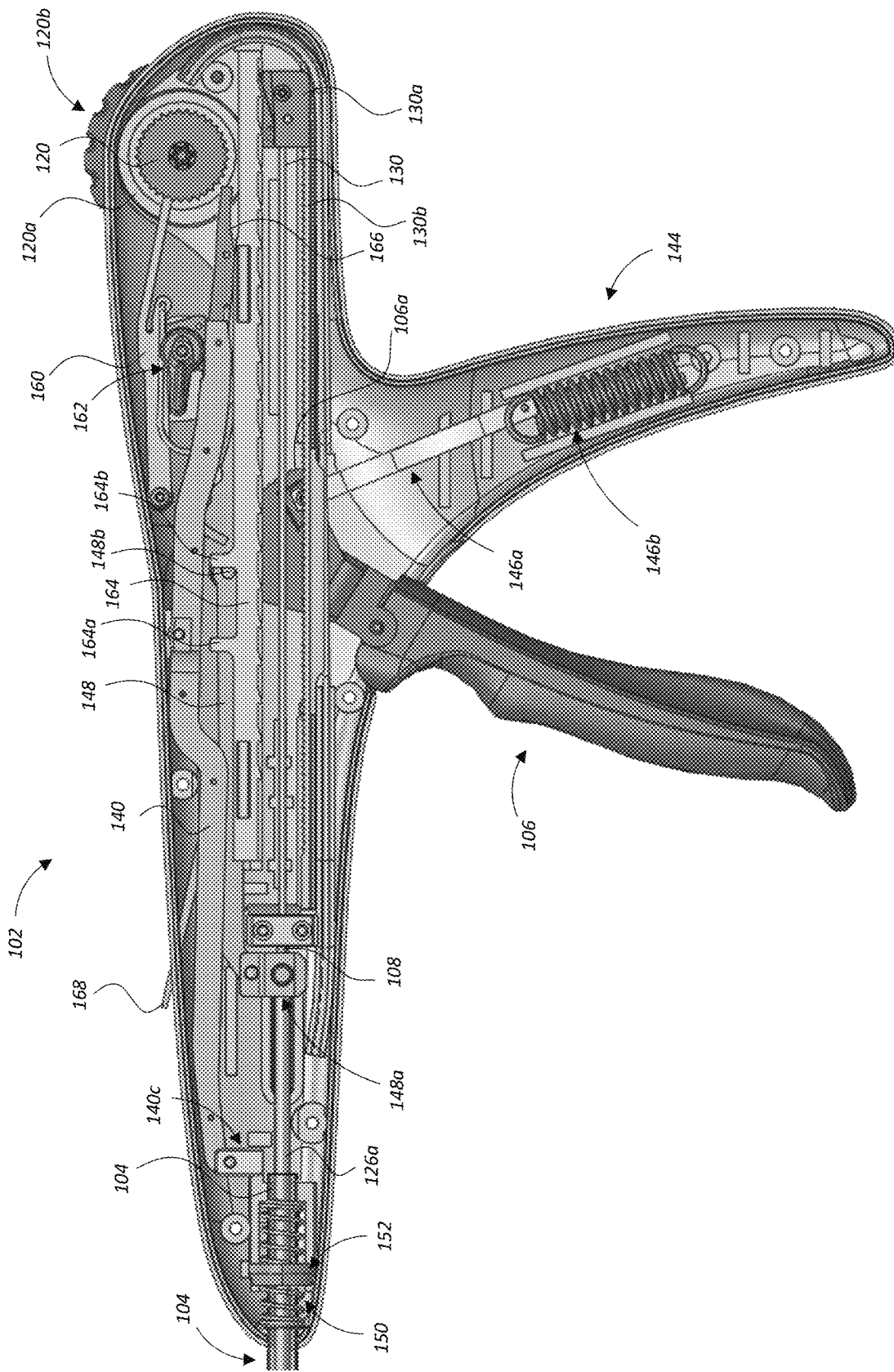

Optionally, while inserting shaft 104 into the body, a shaft blocking lever 140 may be positioned so as to block the shaft from retracting into handle 102; a distal side of shaft blocking lever 140 is biased downwards using a spring, so that a shaft blocker 140c assumes a position being the proximal end of shaft 104, blocking its movement in the proximal direction. A spring 150 may exert force on shaft 104 to push it in the distal direction. This state of handle 102 is shown in FIG. 2C. This figure shows the same elements of FIG. 2B, but at a different state.

Distal opening 104a of shaft 104 may then be pressed against the tissue, in a location where the surgeon wishes to deploy a first one of anchors 112. In a hernia defect closure procedure, distal opening 104a of shaft 104 may be pressed against the peritoneum, a few millimeters up to a few centimeters from the defect.

Referring now to FIG. 2C, the surgeon operates handle 102 to activate the advancement mechanism, so as to expose a distal portion of needle 112 out of distal opening 104a of shaft 104, such that edge 110 of needle 108 penetrates the abdominal wall tissue. This operation of handle 102 may first include bringing shaft blocking lever 140 to its up position, which raises shaft blocker 140c from behind shaft, allowing the shaft to retract further into the handle. Shaft 104 is retracted against the force of spring 150, so that, if the surgeon releases the pressure of apparatus 100 against the tissue, the shaft will return to cover the exposed end of needle 108, thus preventing potential damage to nearby tissues. Optionally, the penetration depth may be adjusted by rotating a nut 152, which limits how far shaft 104 can retract into handle 102.

Then, the advancement mechanism pushes pushrod 126 distally, in a force sufficient to push stopper 128 out of the distalmost anchor's 108 way, and cause that anchor to penetrate the tissue. This involves pressing trigger 106 (the depressed position of the trigger is not shown in the figures), which moves a connecting rod 148 distally, which moves distally a connector 148a that is attached to push tube 126a. Push tube 126a, in turn, pushes pushrod 126 distally.

When connecting rod 148 is moved distally, it also moves a ratcheted rack 164 distally, by a pin 148b that pushes forward a front protrusion 164a of the rack. One of the teeth of ratcheted rack 164 engages a base 130a of advancer rod 130, and therefore advances advancer rod 130. Each full trigger 106 stroke moves forward push tube 126a and pushrod 126 to a length equal to the length travelled by pin 148b, and advancer rod 130 by one increment. The distance between every two adjacent teeth of ratcheted rack 164 is optionally equal to the length of each of anchors 112, such that advancer rod 130 pushes forward, with each increment, exactly the length of one anchor.

Figure 2D:
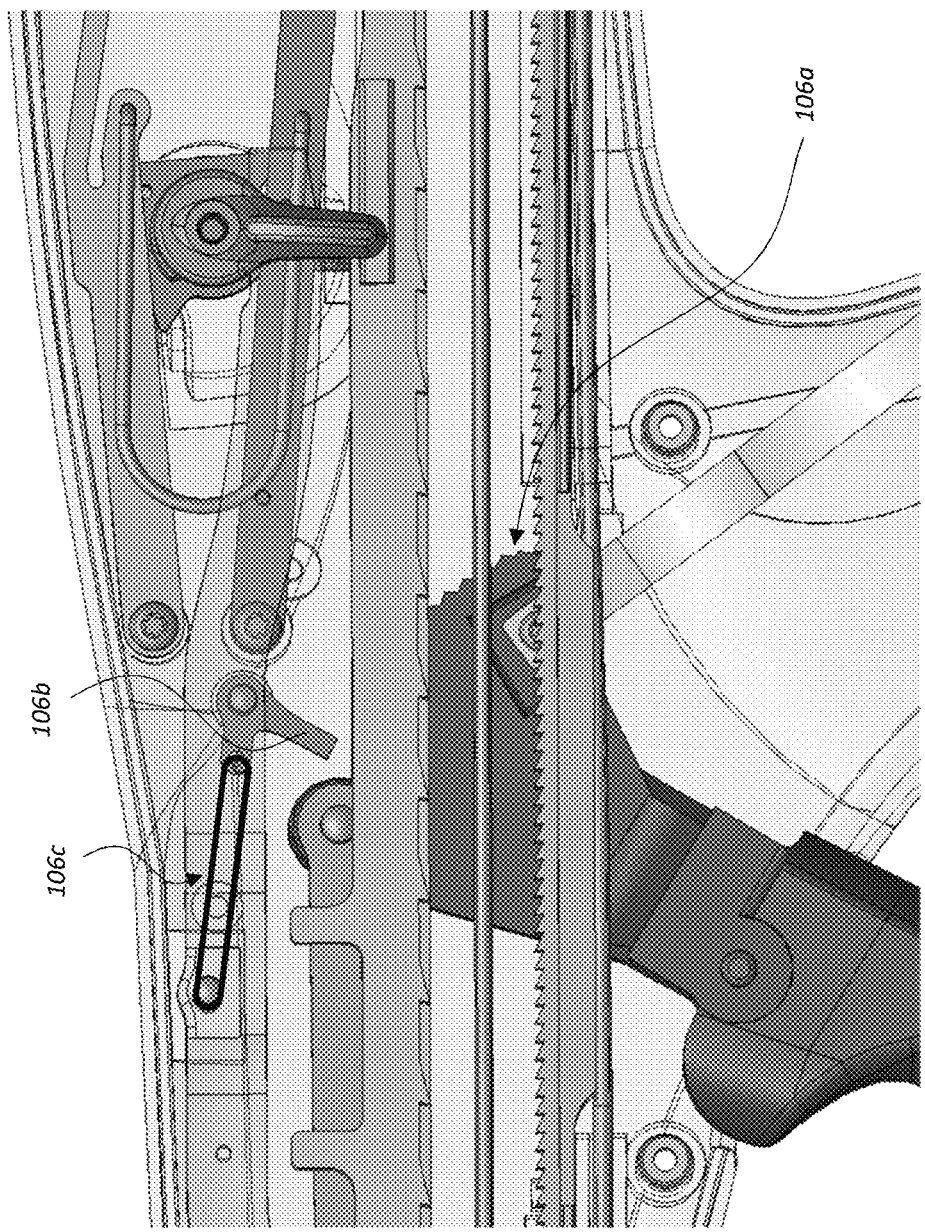

Trigger 106 optionally has a ratcheted surface 106a at its upper end, which engages a tooth 106b biased by a rubber band or spring 106c (better shown in FIG. 2D, in which shaft blocking lever 140 is semi-transparent) when as the trigger is being pressed. This way, even if the surgeon ceases to press trigger 106 before completing a full stroke, the trigger remains in place and does not pop back out; it is held in place by tooth 106b. When a full stroke of trigger 106 is completed, ratcheted surface 106a moves forward away from tooth 106b, and the tooth disengages the ratcheted surface. Trigger 106 is then released, and tooth 106b slides over ratcheted surface 106a and allows the trigger to assume its original position.

When trigger 106 is released after a full stroke, a spring 146a that connects it to the handle's housing pulls the top part of the trigger downwards, causing the trigger itself to move forward, to its original position. Connecting rod 148 returns backwards and retracts pushrod 126 with it, while the backwards retraction of ratcheted rack 164 does not move advancer rod 130 backwards, despite the fact pin 148b pushes a rear protrusion 164b of ratcheted rack 164 backwards; the respective tooth of the ratcheted rack slides over base 130a and does not move it. A ratcheted bar 130b affixed to the housing of handle 102 ensures that base 130a cannot move backwards but only forward; a bottom area of base 130a includes a protrusion (not seen in this view) that suitably engages the ratcheted bar.

The rotation of spool 120a may be controlled by a cam shaft 162 that alternates between two positions: one which (a) pushes a top stopper 160 upwards and disengages it from a ratchet wheel 120 of spool 120a and (b) allows a bottom stopper 166 to move upwards and engage the ratchet wheel; and one which does the reverse, and optionally also pushes down the proximal side of shaft blocking lever 140, such that its distal side rises and unblocks shaft 104 from retracting into handle 102. The second position of cam shaft 162 may be selected by the surgeon after pressing the distal end of shaft 104 onto tissue, and in preparation for retracting the shaft so that needle 108 penetrates the tissue. In addition or as an alternative to controlling shaft blocking lever 140 from cam shaft 162, it may be controlled by pressing and depressing a button 168 that directly presses and depresses, respectively, the distal side of the shaft blocking lever.

Each position of cam shaft 162 prevents rotation of spool 120a in one direction, and allows its rotation in the opposite direction. This allows the surgeon to control the release and retraction of the thread as necessary. Furthermore, the surgeon may utilize a knob 120b of spool 120a to manually rotate the spool in either direction, if the position of cam shaft 162 is suitably set.

Optionally, top stopper 160 is flexible so to allow rotation of spool 120a in both directions while making a clicking sound as its edge bounces on the toothed surface of the spool, providing auditory feedback to the surgeon on the rotation of the spool.

Simultaneously, thread 118 is optionally pulled from its distal free end, to further aid anchor 112 to reach an approximately perpendicular posture, or at least a posture which places the anchor's central axis at 30 degrees or more off the central axis of shaft 104. FIGS. 4A-4C show this stage (in cross sectional non-cross sectional views), with the distalmost anchor 112 out of needle 108 and slightly tilted downwards. Pushrod 126 is shown passing through the distalmost aperture 124, and extending to a distance of, for example, 5 to 30 mm from edge 110 of needle 108. The pushing of anchor 112 (and the optional pulling of thread 118) may continue until anchor 112 assumes an approximately perpendicular position inside the tissue (this position is not shown in FIGS. 4A-4C).

After successfully deploying the distalmost anchor 112, the advancement mechanism may retract needle 108 into shaft 104 and pushrod 126 into needle 108, and the surgeon may move apparatus 100 to a next location in which anchor deployment is desired. FIG. 5 shows needle 108 and pushrod 126 back in their original locations inside shaft 104, ready to deploy the next one of anchors 112. The surgeon may then reposition the shaft, and repeat operating handle 102, in the manner described above, to deploy the next one of anchors 112. This may be repeated until a desired number of anchors 112 has been deployed.

In a hernia defect closure procedure, the anchors may be deployed in such locations and such order to form a suitable pattern of tissue closure.

Reference is now made to FIG. 6A, which schematically illustrates three exemplary anchors 112 that were deployed in the abdominal wall. As shown, anchors 112 each assume an approximately perpendicular posture inside the tissue. In a hernia defect closure procedure, anchors 112 may be deployed, for example, into the muscle layer of the abdominal wall, and reside at a depth of, for example, 44 mm to 25 mm inside the abdominal wall, as measured from the fascial direction.

Since thread 118 was threaded through rings 116 when anchors 112 were inside apparatus 100, they remain threaded therethrough also after deployment of the anchors. A distal end of thread 118 is also ejected from apparatus 100, and the two ends 118a of the thread may be manually pulled together, which in turn pulls rings 116 and brings anchors 112 closer to each other. This is shown in FIG. 6B, in which anchors 112 are closer to one another, and the two ends of thread 118 are secured together using a securing element 132. Alternatively, the two ends of thread may be simply knotted. The pulling the two ends 118a of the thread may further contribute to the anchors' 112 movement towards an approximately perpendicular posture.

As an alternative to pulling together the two ends 118a of the thread, a locking anchor may be deployed as the first and/or last anchor in the series. A locking anchor deployed as the first anchor may include a unidirectional or bidirectional locker, that prevents the thread from sliding unidirectionally or bidirectionally through the anchor. A locking anchor deployed as the last anchor may include a unidirectional locker, that allows only a tightening of the suture, e.g., to close the hernia defect. As an alternative to deploying such locking anchors into tissue, they may be only deployed over the thread but not in the tissue, such that their bodies, which are larger than the rings of the other anchors, are stopped at the rings. They may therefore be referred to simply as "lockers".

Figure 11B:
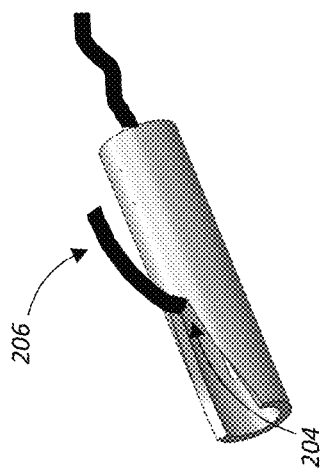
FIG. 11B is a perspective view of a bidirectional locking anchor, in accordance with an embodiment.
Figure 11A:
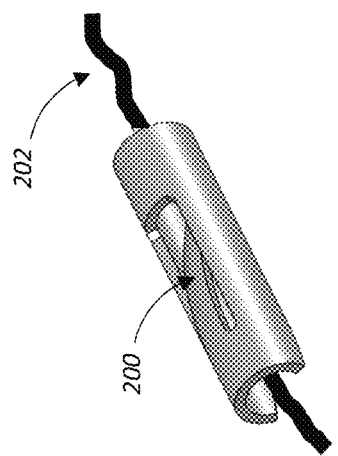
FIG. 11A is a perspective view of a unidirectional locking anchor, in accordance with an embodiment.

Reference is now made to FIG. 11A, which shows an exemplary unidirectional locking anchor. This anchor is structured as a tube, similar to anchor 112 of the previous figures, but has a tooth 220 that is bent inwardly, into the anchor's lumen. When a thread 202 is threaded through this anchor, a free end (not shown) of tooth 200 contacts the thread, and prevents it from moving to the left side of the anchor. If thread 202 is pulled to the right, however, it will easily slide over the free end of tooth 200.

Reference is now made to FIG. 11B, which shows an exemplary bidirectional locking anchor. This anchor utilizes a locking slit 204 to prevent a thread 206 engaged in the slit from moving to either direction. Slit 204 may have a tapered shape, such that, when the left end of thread 206 is pulled backwards, towards the right end of the thread, the thread gradually enters deeper and deeper into the slit, until reaching very close to its end. There, the tapered shape of slit 204 presses on thread 206, slightly compressing it at the contact area, and thus preventing its movement in any direction. Slit 204 is optionally tapered along its entire length. The tapering is optionally uniform along the entire length of slit 204, or varies along this length. Advantageously, if slit 204 is tapered until its very end, thread 206 will tear if pulled with excessive force; the two sides of the slit will simply cut deeply into the thread until it rips. This serves as a safety mechanism, because the tearing of thread 206 under excessive tension will prevent the locking anchor from being pulled out of the tissue, severely damaging it.

Those of skill in the art will recognize that various other locking means may be employed at either side of a thread, to prevent the need to manually form a knot between the two opposing ends of the thread.

Figure 12A:
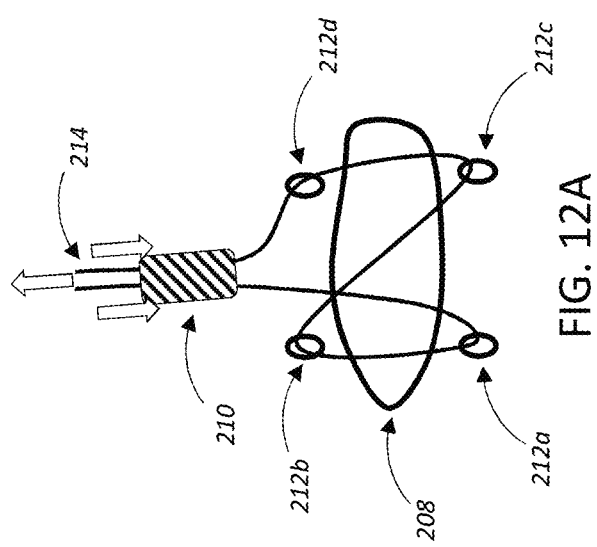
FIGS. 12A and 12B illustrate defect closure with a bidirectional locker, in accordance with an embodiment.
Figure 12B:
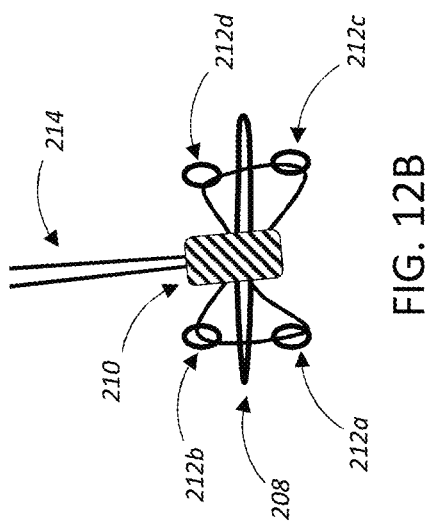

Reference is now made to FIGS. 12A and 12B, which show an example of utilizing a unidirectional locker in a defect 208 closure task. In FIG. 12A, four anchors (represented by their rings 212) are deployed in tissue in the following order: 212a, 212b, 212c, and 212d. A locker 210 is then positioned over the two ends of a thread 214. Locker 210 is the slid over thread 214 while pulling the ends of the threads away. This results in the arrangement shown in FIG. 12B, where rings 212 are brought closer together, defect 208 is closed, and thread 214 is tightly held by locker 210.

Figure 13A:
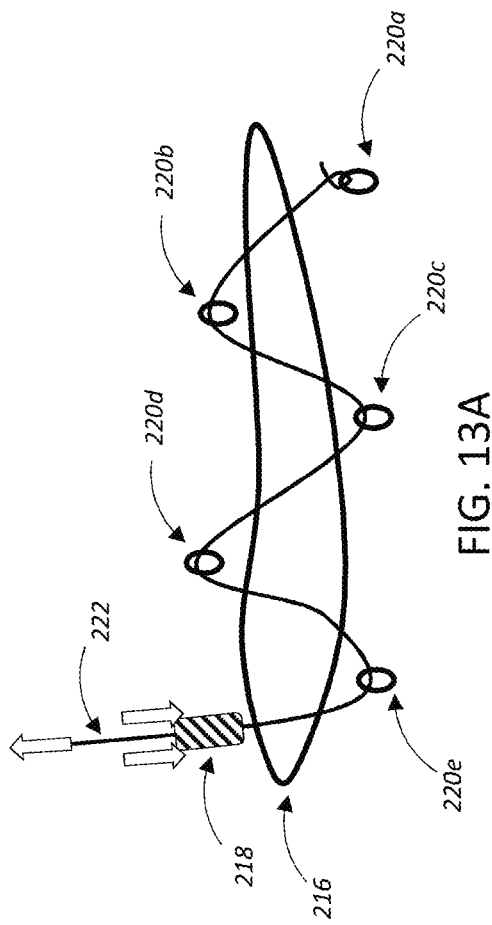
FIGS. 13A and 13B illustrate a different defect closure with a bidirectional locker, in accordance with an embodiment.
Figure 13B:
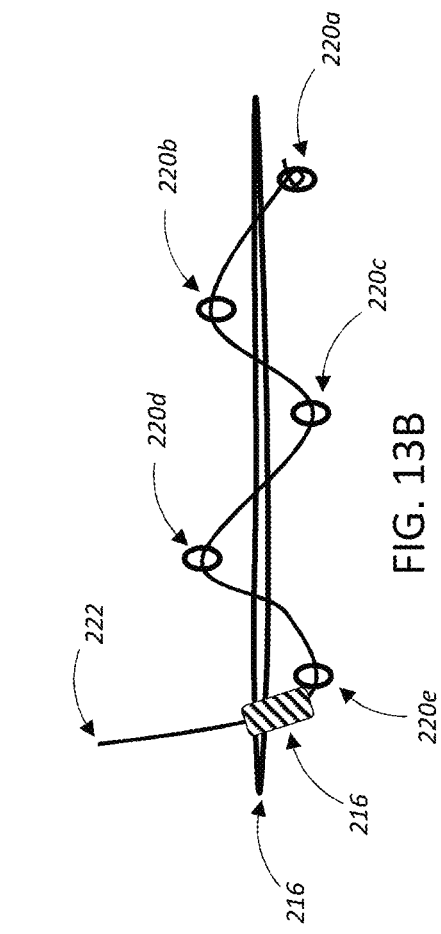

Reference is now made to FIGS. 13A and 13B, which show another example of utilizing a unidirectional locker in a defect 216 closure task. In FIG. 13A, five anchors (represented by their rings 220) are deployed in tissue in the following order: 220a, 220b, 220c, 220d, and 220e. A thread 222 is optionally tied to the ring 220a of the first-deployed anchor. Alternatively, a locking anchor may be the first-deployed anchor, such that no tying is required. Further alternatively, a stopper (not shown) may be attached to the end of thread 222 near ring 220a, such that the thread cannot detach from rings 220a. This may be, for example, a T-shaped bar whose leg is attached to the thread, and whose top shoulders are wider than the diameter of the ring and hence cannot escape it.

After deploying the last anchor, a unidirectional locker 216 is positioned over the free end of thread 222. Locker 216 is the slid over thread 222 while pulling the end of the thread away. This results in the arrangement shown in FIG. 13B, where rings 220 are brought closer together, defect 216 is closed, and thread 222 is tightly held by locker 216.

Figure 14B:
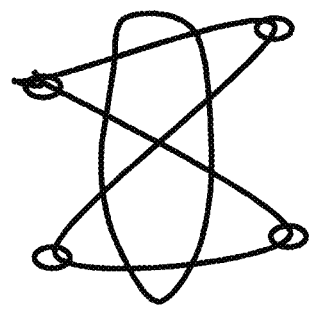
FIGS. 14A, 14B, and 14C illustrate different suturing patterns, in accordance with embodiments.
Figure 14C:
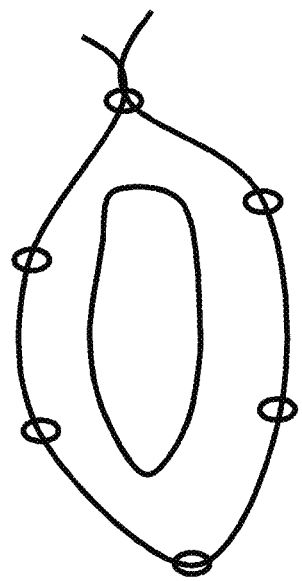
Figure 14A:
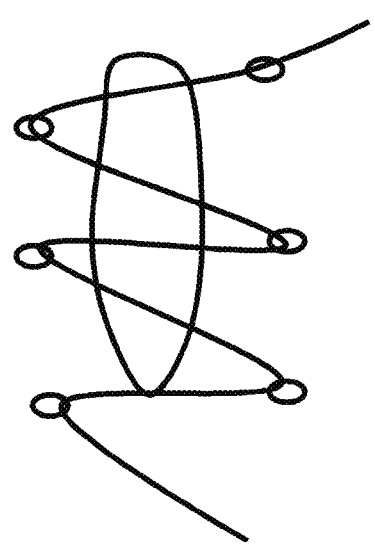

Reference is now made to FIGS. 14A-14C, which show a number of exemplary suturing patterns using the present apparatus. Each of these figures shows a defect, a suture, and multiple rings of implanted anchors (that are not shown). FIG. 14A shows a Z-shape pattern, FIG. 14B shows and X-shape pattern, and FIG. 14C shows a purse string pattern.

Figure 15:
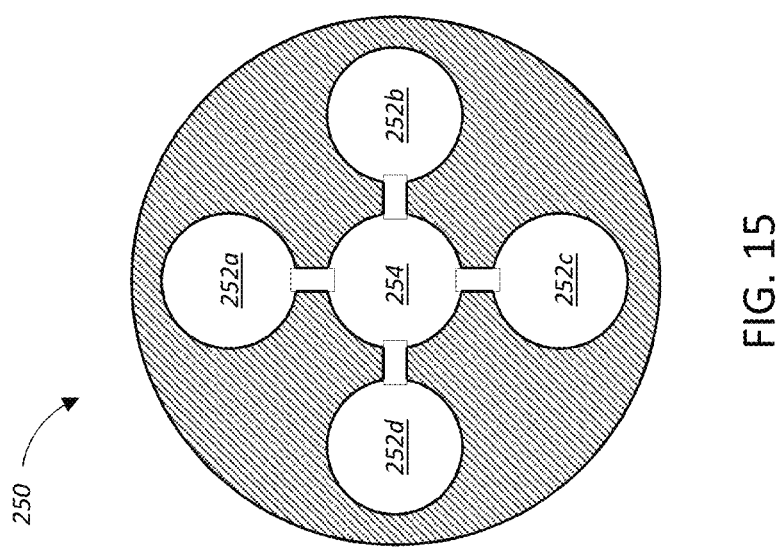
FIG. 15 is a cross-sectional view of a multi-lumen shaft, in accordance with an embodiment.

Reference is now made to FIG. 15, which shows a variant of apparatus 100, in which, instead of a single needle housed in a shaft, there is a multi-lumen shaft 250 that houses multiple needles. In this example, there are four lumens 252a-d that can accommodate four needles (not shown), but a different number of lumens and needles, such as between 2 and 8, is explicitly intended herein. A central lumen 254 is also provided, which can contain the loops of the anchors positioned in the needles in lumens 252a-d. Each of lumens 252a-d also accommodates the other components acting together with the needle, such as a pushrod, an advancer rod, a push tube, etc. (all not shown).

An apparatus with a multi-lumen shaft 250 may contain a relatively large number of anchors, so that the apparatus does not need to be extracted from the body often to refill anchors or switch to another, full, apparatus.

Figure 16:
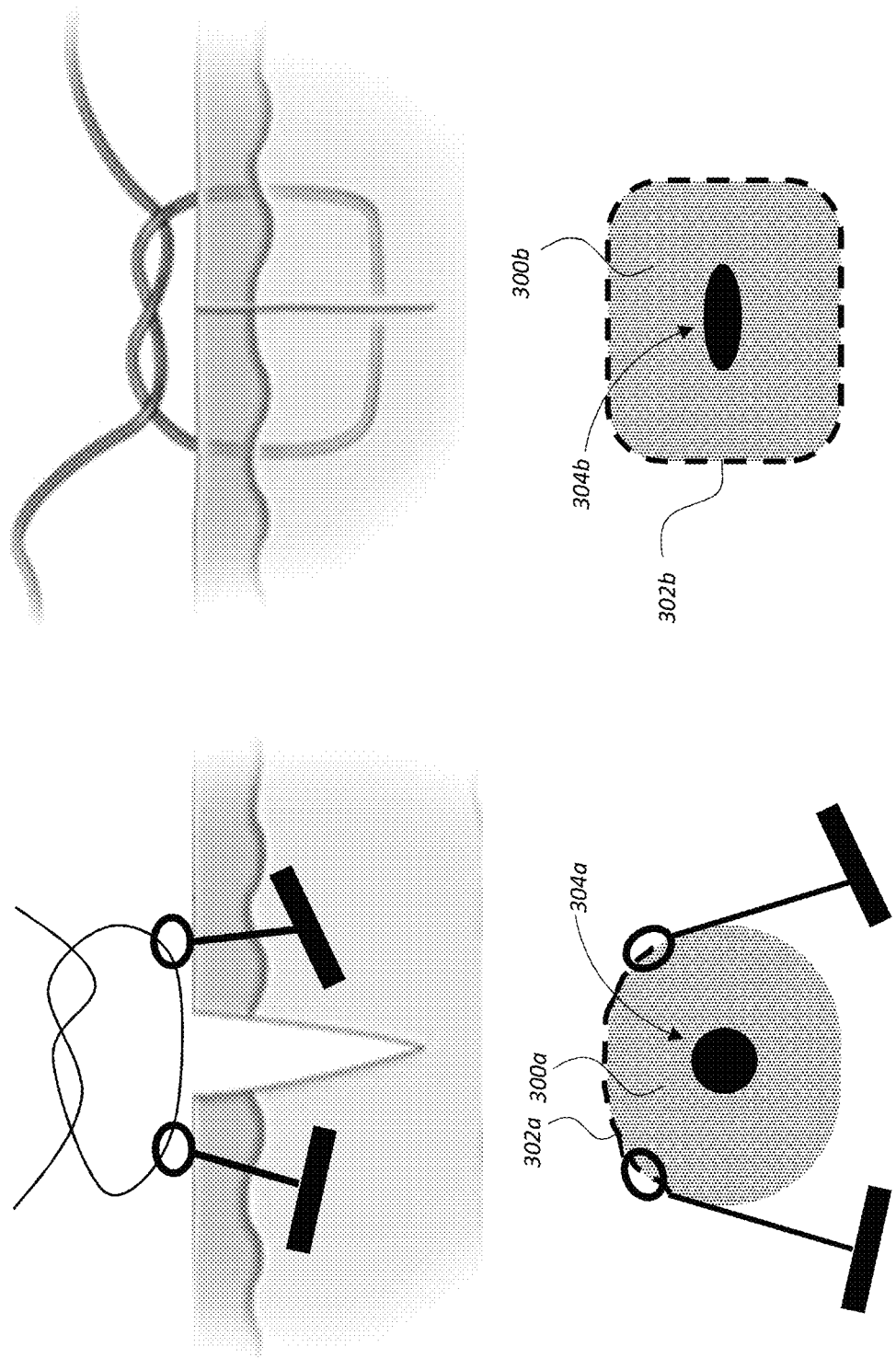
FIG. 16 is an illustration of nerve or blood vessel entrapment, in accordance with an embodiment.

Reference is now made to FIG. 16, which illustrates how closing a defect with the present apparatus prevents nerve and/or blood vessel entrapment, compared with standard manual suturing.

At the top left of the figure, two anchors of the present invention are shown implanted in tissue on opposing sides of a defect, and a thread is used to approximate their loops and close the defect.

The bottom left of the figure illustrates a nerve or a blood vessel 304a in tissue 300a, enclosed between the two anchors and a thread 302a that connects them. Vessel 304a stays substantially intact, because there is only minimal pressure applied to tissue 300a by the wires of the anchors, and because the thread that connects the rings at the ends of these wires also applies minimal pressure to the tissue.

In contrast, when closing a defect by manual suturing with a surgical suture, as shown on the right top and right bottom of the figure, the tightened suture 302b presses radially on the tissue 300b are causes deformation, entrapment, or even closure of a nerve or a blood vessel 304b.

Experimental Results

Figure 7:
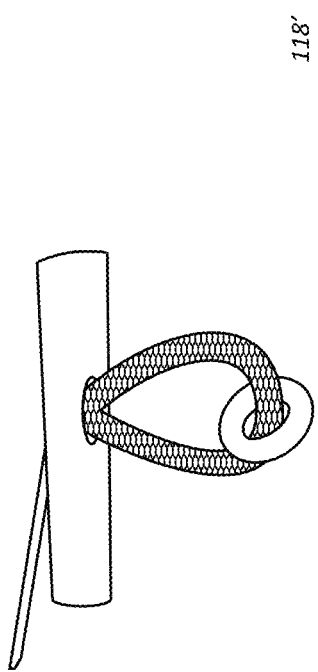
FIG. 7 illustrates an experimental anchor.

The inventors have tested an experimental apparatus, which was substantially identical to the apparatus disclosed here, on a sacrificed pig. An illustration of the anchor used in the test is shown in FIG. 7. FIGS. 8A-8E, in turn, show photographs of different stages of the test.

Figure 8E:
FIGS. 8A-8E are photographs of five stages of an experiment performed by the inventors.
Figure 8D:
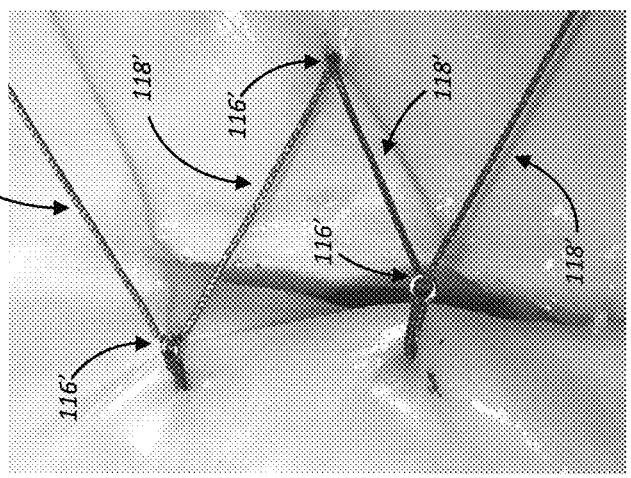

A hernia defect was emulated by forming an approximately 40 mm-long tear 134' in the animal's abdominal wall. In FIG. 8A, the shaft 104' of the experimental apparatus is shown being pushed against the fascia in a first location. The free portion of the thread which exits the shaft is shown taught, as it was pulled aside by the tester. FIG. 8B shows the apparatus being pulled back after successful deployment of a first anchor. The free portion of the thread is now shown at the left side of the photo, and the portion that enter the shaft on the right side of the photo. The ring of the first anchor is shown at 116'.

Figure 8C:
Figure 8B:
Figure 8A:
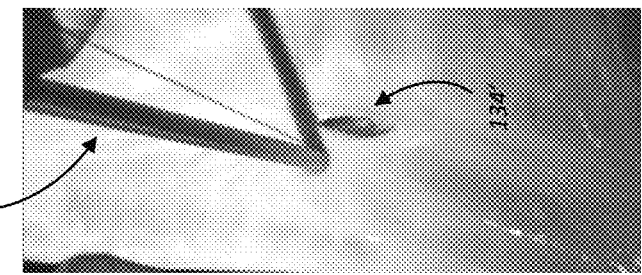

In FIG. 8C, the apparatus has been repositioned at the next location, now to the right of the tear. A second anchor was deployed at that location. Next (no photograph provided), a third anchor was deployed at the left side of the tear, at a certain distance from the first anchor.

FIG. 8D, which is a photograph taken at a larger magnification, shows the thread 118' extending between the three respective rings 116' of the deployed anchors.

FIG. 8E shows the tear closed, after the thread was pulled and tensioned, and the two edges of the tear were brought together by the anchors implanted laterally to the tear. The two edges of the thread were knotted in a central location between the rings.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the description and claims of the application, each of the words "comprise" "include" and "have", and forms thereof, are not necessarily limited to members in a list with which the words may be associated. In addition, where there are inconsistencies between this application and any document incorporated by reference, it is hereby intended that the present application controls.

What is claimed is:

1. An apparatus for tissue approximation, comprising:
   a needle having an opening, the needle housing multiple anchors in a single file, wherein each of said anchors comprises:
   an elongated tubular body,
   a loop connected to said elongated tubular body, wherein the apparatus further comprises a thread that is threaded sequentially through the loops, and
   a fin emerging outwardly from said elongated tubular body; and
   a pushrod configured to separately push each of said anchors, by its fin, towards the opening of said needle, to extract each respective anchor from the opening;
   wherein said pushrod is sized to push each of said anchors until the respective anchor completely exits the opening of said needle.

2. The apparatus according to claim 1, further comprising an elongated shaft, wherein said needle is disposed inside said elongated shaft.

3. The apparatus according to claim 2, further comprising a handle disposed at a proximal end of said elongated shaft.

4. The apparatus according to claim 3, wherein said pushrod is triggerable by said handle to push each of said anchors.

5. The apparatus according to claim 4, further comprising a push tube disposed inside said elongated shaft and over said needle, wherein said pushrod is attached to a distal end of said push tube, and wherein the triggering of the pushrod is by pushing said push tube distally.

6. The apparatus according to claim 5, wherein said handle comprises a trigger that is connected to a proximal end of said push tube.

7. The apparatus according to claim 3, wherein said handle is configured to allow said elongated shaft to retract into said handle while maintaining said needle stationary, so that a distal area of said needle is exposed and is able to penetrates tissue.

8. The apparatus according to claim 7, wherein said handle comprises a shaft blocking lever that is movable between a position that blocks backwards movement of said shaft and a position that allows backwards movement of said shaft.

9. The apparatus according to 3, wherein said thread is rolled, at its proximal area, over a spool of thread comprised in the handle.

10. The apparatus according to claim 1, wherein:
    said needle has an aperture disposed at a distal area of said needle;
    said pushrod is flexible and is configured to bend when passing through said aperture to push each of said anchors,
    said pushrod is configured to push each of said anchors by contact between a distal end of said pushrod and the fin of the respective anchor, and
    the fin of the most distal anchor in the single file protrudes from said needle through said aperture.

11. The apparatus according to claim 2, wherein said needle has an elongated slit which opens to a distal end of said needle.

12. The apparatus according to claim 11, wherein said loops of said anchors exit said needle through said elongated slit to a space between said needle and an inner wall of said elongated shaft.

13. The apparatus according to claim 1, wherein each fin of each of said anchors emerges from said elongated tubular body opposite said loop of each of said anchors.

14. A method for tissue approximation, comprising:
provided the apparatus of claim 1;
operating a handle to trigger said pushrod to perform the separate pushing of each of said anchors, so as to deploy at least some of said anchors in the tissue;
pulling said thread, thereby approximating said loops, approximating said anchors, and approximating the tissue; and
securing said thread by: deploying a locker over said thread, or knotting two ends of said thread together.

* * * * *